(12) United States Patent
Shoham et al.

(10) Patent No.: US 8,858,929 B2
(45) Date of Patent: Oct. 14, 2014

(54) OPTICALLY SENSITIVE CELL NETWORK

(71) Applicant: Technion Research & Development Foundation Ltd., Haifa (IL)

(72) Inventors: Shy Shoham, Haifa (IL); Anat Marom, Kiryat-Bialik (IL); Sanjeev Kumar Mahto, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 13/733,163

(22) Filed: Jan. 3, 2013

(65) Prior Publication Data

US 2013/0171116 A1 Jul. 4, 2013

Related U.S. Application Data

(60) Provisional application No. 61/582,909, filed on Jan. 4, 2012.

(51) Int. Cl.
*A61K 48/00* (2006.01)
*A61L 27/38* (2006.01)
*A61L 27/52* (2006.01)
*C12N 5/0793* (2010.01)
*A61N 5/06* (2006.01)

(52) U.S. Cl.
CPC ............... *A61L 27/383* (2013.01); *A61L 27/52* (2013.01); *A61F 2230/0063* (2013.01); *C12N 5/062* (2013.01); *A61N 5/0622* (2013.01); *C12N 2510/00* (2013.01)
USPC ...... 424/93.21; 424/93.1; 424/93.2; 424/422; 424/423

(58) Field of Classification Search
None
See application file for complete search history.

(56) References Cited

PUBLICATIONS

Cullen et al. Critical Rev Biomed Engineering 2011;39:201-40.*
Wen et al. PloS One 2010;5:e12893, pp. 1-13.*
Xie et al. Tissue Engineering 2001;7:585-98.*
Yamamoto et al. Adv Drug Delivery Rev 2006;58:535-54.*
Wikipedia, Shear Modulus, Last modified Jun. 2013.*
Lee et al. Macromolecules 2000;33:4291-4.*
Luo et al. Acta Biomaterialia 2012;8:734-43.*
Sarig-Nadir et al. "Laser Photoablation of Guidance Microchannels Into Hydrogels Directs Cell Growth in Three Dimensions", Biophysical Journal, 96: 4743-4752, Jun. 2009.
Bogomolova "Transparent Polymer Implant Delivers Light Signals Deep Within Body", Polymer Solutions Incorporated, 2 P., 2014.
Kato-Negishi et al. "Fabrication of Transplantable 3D-Neuronal Network", 14th International Conference on Miniaturized Systems for Chemistry and Life Sciences, Groningen, The Netherlands, Oct. 3-7, 2010, p. 632-634, 2010.

* cited by examiner

*Primary Examiner* — Janice Li

(57) ABSTRACT

A neural network is disclosed. The neural network comprises a plurality of optogenetically modified neural cells being three-dimensionally distributed in a hydrogel medium and being disconnected from any solid support having a shear modulus above 1 GPa.

23 Claims, 22 Drawing Sheets
(18 of 22 Drawing Sheet(s) Filed in Color)

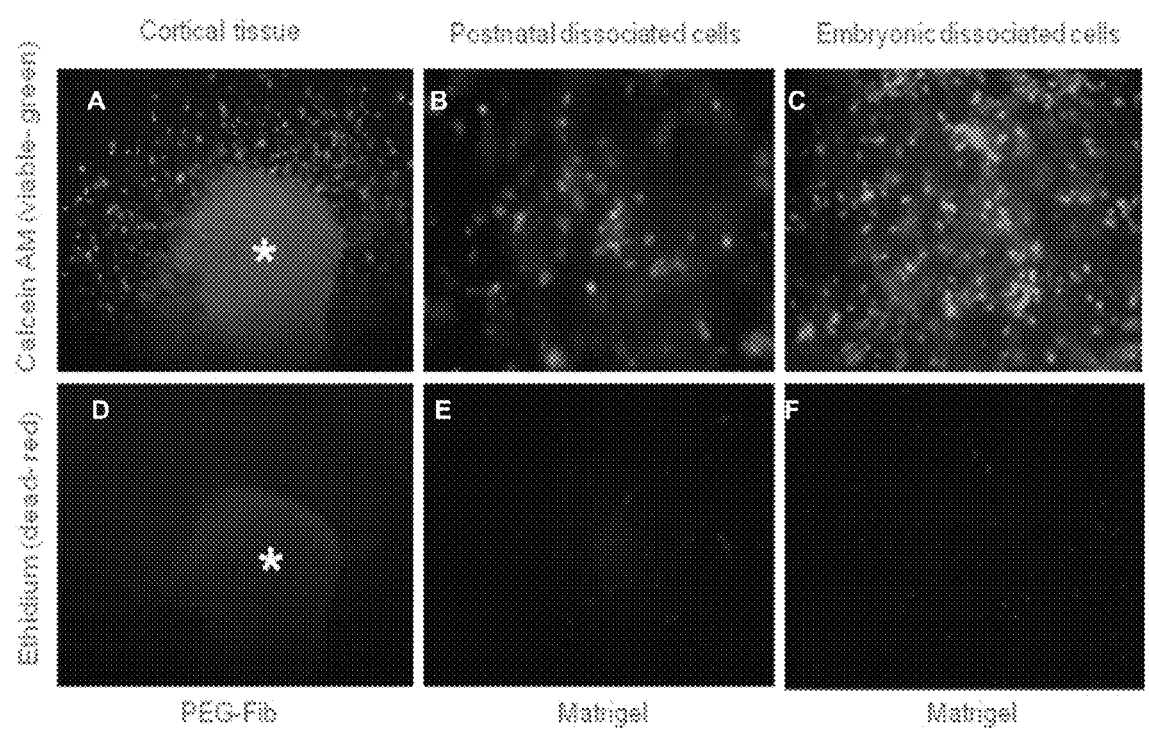
FIGs. 11A-F

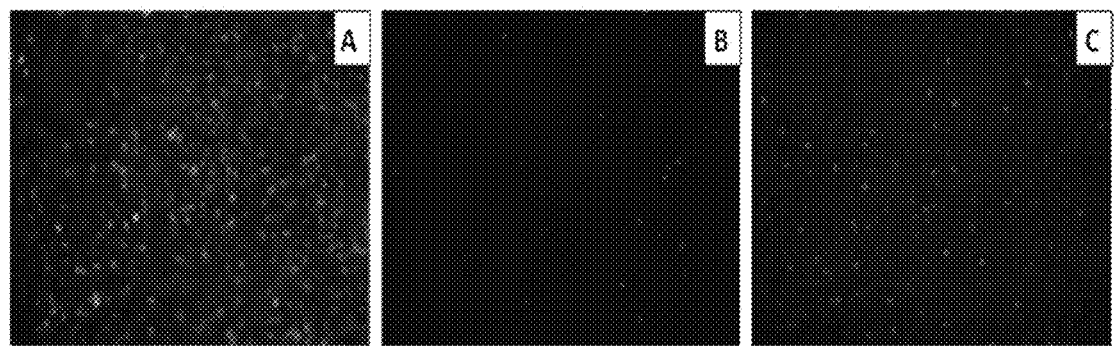
FIGs. 12A-C

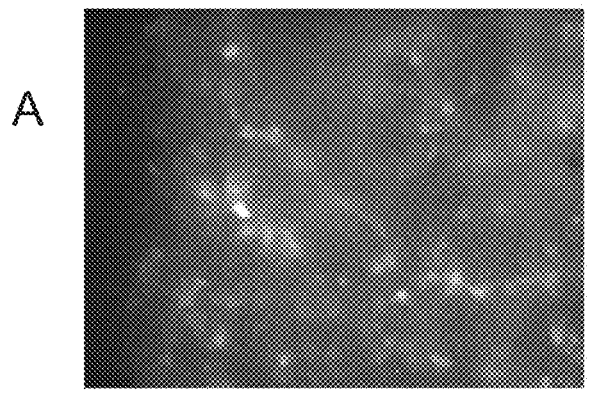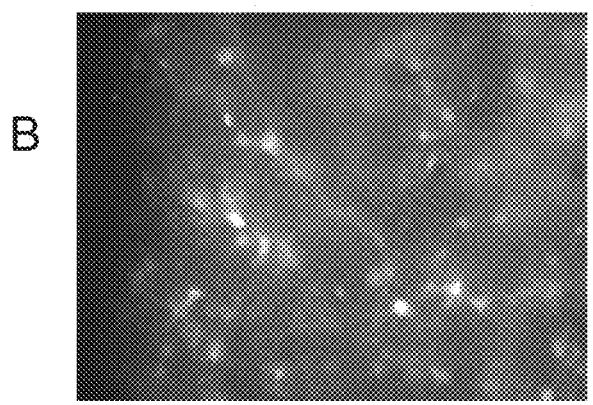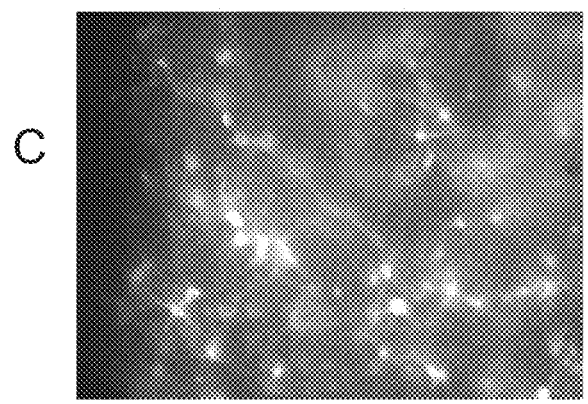
FIGs. 13A-C

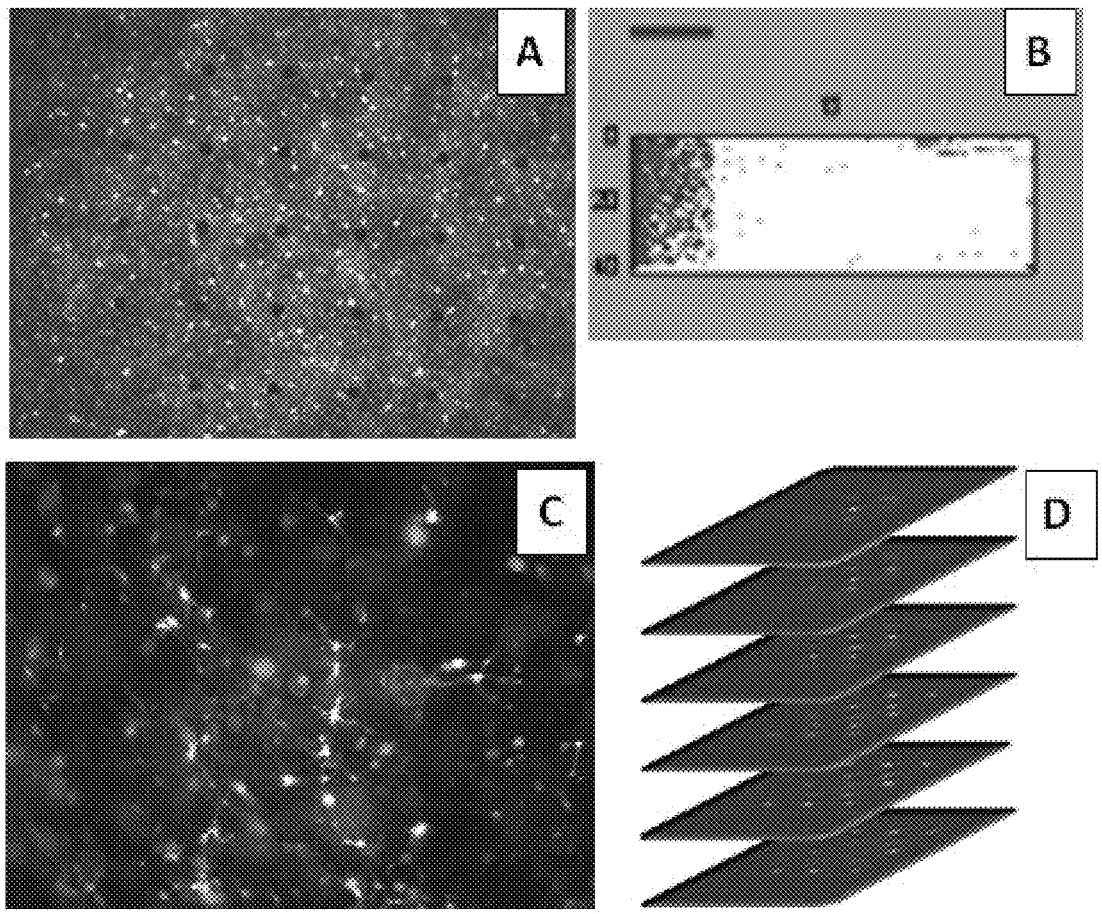
FIGs. 15A-D

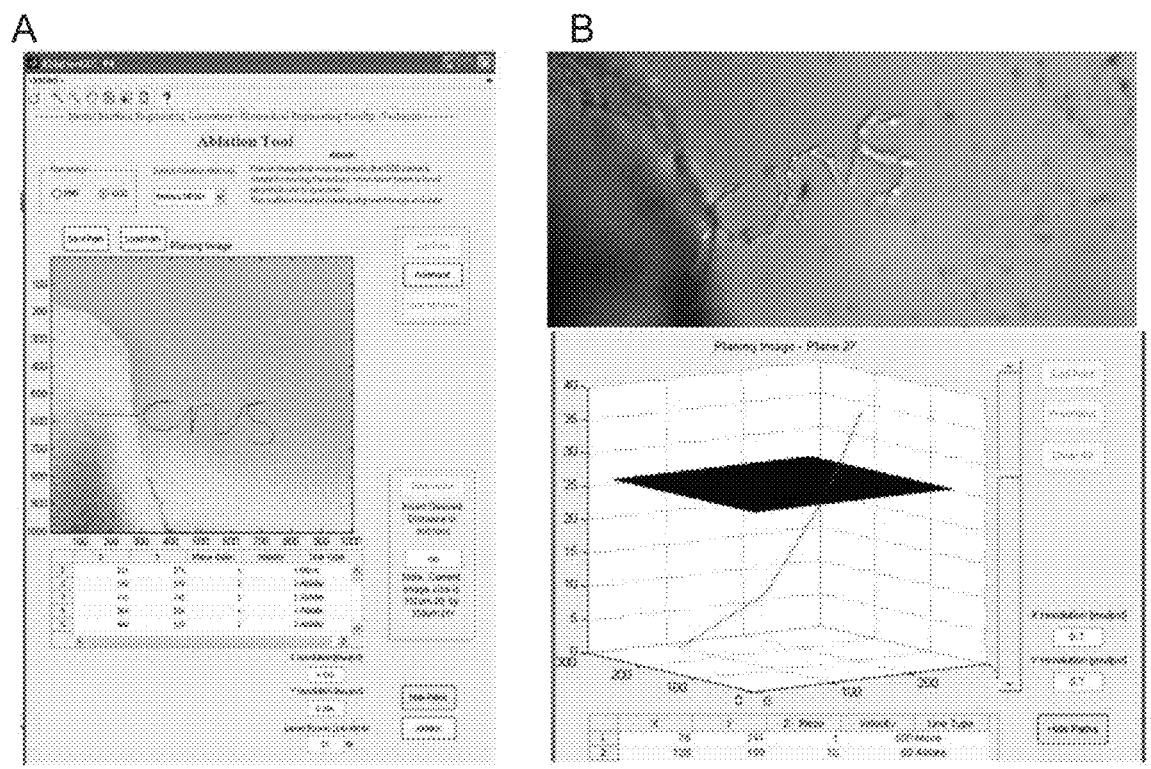
FIGs. 16A-B

FIGs. 20A-D

```
                        SEQUENCE LISTING

<160> NUMBER OF SEQ ID NOS: 5

<210> SEQ ID NO 1
<211> LENGTH: 257
<212> TYPE: PRT
<213> ORGANISM: Uncultured marine bacterium HF10_19P19

<400> SEQUENCE: 1

Met Ser Ile Ile Lys Ser Leu Lys Ser Val Ala Ile Ala Ser Leu Ala
1               5                   10                  15

Ile Leu Ile Pro Ser Ile Ala Leu Ala Ala Gly Gly Asn Leu Glu Pro
            20                  25                  30

Asn Asp Pro Val Gly Ile Thr Phe Trp Leu Ile Ser Ile Ala Met Val
        35                  40                  45

Ala Ala Thr Val Phe Phe Leu Met Glu Ser Leu Arg Val Asp Gly Lys
    50                  55                  60

Trp Arg Thr Ser Met Ile Val Gly Gly Leu Val Thr Leu Val Ala Ala
65                  70                  75                  80

Val His Tyr Phe Tyr Met Arg Asp Val Trp Val Ala Thr Gly Ala Ser
                85                  90                  95

Pro Thr Val Phe Arg Tyr Val Asp Trp Leu Ile Thr Val Pro Leu Gln
            100                 105                 110

Met Ile Glu Phe Tyr Leu Ile Leu Ala Ala Cys Thr Ala Ile Ala Val
        115                 120                 125

Gly Val Phe Trp Arg Leu Met Ile Gly Thr Met Val Met Leu Ile Gly
    130                 135                 140

Gly Tyr Leu Gly Glu Ala Gly Phe Ile Asn Ala Thr Val Gly Phe Val
145                 150                 155                 160

Ile Gly Met Ala Gly Trp Gly Tyr Ile Leu Tyr Glu Ile Phe Ala Gly
                165                 170                 175

Glu Ala Gly Lys Val Ala Ala Glu Gly Ala Pro Pro Ser Val Gln Ser
            180                 185                 190

Ala Phe Asn Thr Met Arg Leu Ile Val Thr Ile Gly Trp Ala Ile Tyr
        195                 200                 205

Pro Leu Gly Tyr Phe Phe Gly Tyr Met Thr Gly Gly Val Asp Ala Asn
    210                 215                 220

Ser Leu Asn Leu Ile Tyr Asn Val Ala Asp Val Val Asn Lys Ile Gly
225                 230                 235                 240

Phe Cys Leu Ala Ile Trp Ala Ala Ala Thr Ser Gln Ser Glu Ala Ala
                245                 250                 255
```

Lys

```
<210> SEQ ID NO 2
<211> LENGTH: 262
<212> TYPE: PRT
<213> ORGANISM: Halobacterium sp.

<400> SEQUENCE: 2
```

| | | | | | | | | | | | | | | |
|---|---|---|---|---|---|---|---|---|---|---|---|---|---|---|
| Met | Leu | Glu | Leu | Leu | Pro | Thr | Ala | Val | Glu | Gly | Val | Ser | Gln | Ala | Gln |
| 1 | | | | 5 | | | | | 10 | | | | | 15 | |
| Ile | Thr | Gly | Arg | Pro | Glu | Trp | Ile | Trp | Leu | Ala | Leu | Gly | Thr | Ala | Leu |
| | | | 20 | | | | | 25 | | | | | 30 | | |
| Met | Gly | Leu | Gly | Thr | Leu | Tyr | Phe | Leu | Val | Lys | Gly | Met | Gly | Val | Ser |
| | | 35 | | | | | 40 | | | | | 45 | | | |
| Asp | Pro | Asp | Ala | Lys | Lys | Phe | Tyr | Ala | Ile | Thr | Thr | Leu | Val | Pro | Ala |
| | 50 | | | | | 55 | | | | | 60 | | | | |
| Ile | Ala | Phe | Thr | Met | Tyr | Leu | Ser | Met | Leu | Leu | Gly | Tyr | Gly | Leu | Thr |
| 65 | | | | | 70 | | | | | 75 | | | | | 80 |
| Met | Val | Pro | Phe | Gly | Gly | Glu | Gln | Asn | Pro | Ile | Tyr | Trp | Ala | Arg | Tyr |
| | | | | 85 | | | | | 90 | | | | | 95 | |
| Ala | Asp | Trp | Leu | Phe | Thr | Thr | Pro | Leu | Leu | Leu | Asp | Leu | Ala | Leu | Leu |
| | | | 100 | | | | | 105 | | | | | 110 | | |
| Leu | Val | Asp | Ala | Asp | Gln | Gly | Thr | Ile | Leu | Ala | Leu | Val | Gly | Ala | Asp |
| | | 115 | | | | | 120 | | | | | 125 | | | |
| Gly | Ile | Met | Ile | Gly | Thr | Gly | Leu | Val | Gly | Ala | Leu | Thr | Lys | Val | Tyr |
| 130 | | | | | 135 | | | | | 140 | | | | | |
| Ser | Tyr | Arg | Phe | Val | Trp | Trp | Ala | Ile | Ser | Thr | Ala | Ala | Met | Leu | Tyr |
| 145 | | | | | 150 | | | | | 155 | | | | | 160 |
| Ile | Leu | Tyr | Val | Leu | Phe | Phe | Gly | Phe | Thr | Ser | Lys | Ala | Glu | Ser | Met |
| | | | | 165 | | | | | 170 | | | | | 175 | |
| Arg | Pro | Glu | Val | Ala | Ser | Thr | Phe | Lys | Val | Leu | Arg | Asn | Val | Thr | Val |
| | | | 180 | | | | | 185 | | | | | 190 | | |
| Val | Leu | Trp | Ser | Ala | Tyr | Pro | Val | Val | Trp | Leu | Ile | Gly | Ser | Glu | Gly |
| | | 195 | | | | | 200 | | | | | 205 | | | |
| Ala | Gly | Ile | Val | Pro | Leu | Asn | Ile | Glu | Thr | Leu | Leu | Phe | Met | Val | Leu |
| | 210 | | | | | 215 | | | | | 220 | | | | |
| Asp | Val | Ser | Ala | Lys | Val | Gly | Phe | Gly | Leu | Ile | Leu | Leu | Arg | Ser | Arg |
| 225 | | | | | 230 | | | | | 235 | | | | | 240 |
| Ala | Ile | Phe | Gly | Glu | Ala | Glu | Ala | Pro | Glu | Pro | Ser | Ala | Gly | Asp | Gly |
| | | | | 245 | | | | | 250 | | | | | 255 | |
| Ala | Ala | Ala | Thr | Ser | Asp | | | | | | | | | | |
| | | | 260 | | | | | | | | | | | | |

```
<210> SEQ ID NO 3
<211> LENGTH: 250
<212> TYPE: PRT
<213> ORGANISM: Haloterrigena sp.

<400> SEQUENCE: 3
```

| | | | | | | | | | | | | | | |
|---|---|---|---|---|---|---|---|---|---|---|---|---|---|---|---|
| Met | Cys | Cys | Ala | Ala | Leu | Ala | Pro | Pro | Met | Ala | Ala | Thr | Val | Gly | Pro |
| 1 | | | | 5 | | | | | 10 | | | | | 15 | |
| Glu | Ser | Ile | Trp | Leu | Trp | Ile | Gly | Thr | Ile | Gly | Met | Thr | Leu | Gly | Thr |
| | | | 20 | | | | | 25 | | | | | 30 | | |
| Leu | Tyr | Phe | Val | Gly | Arg | Gly | Arg | Gly | Val | Arg | Asp | Arg | Lys | Met | Gln |
| | | 35 | | | | | 40 | | | | | 45 | | | |
| Glu | Phe | Tyr | Ile | Ile | Thr | Ile | Phe | Ile | Thr | Thr | Ile | Ala | Ala | Ala | Met |

```
                    50                  55                  60
Tyr Phe Ala Met Ala Thr Gly Phe Gly Val Thr Glu Val Met Val Gly
 65                  70                  75                  80

Asp Glu Ala Leu Thr Ile Tyr Trp Ala Arg Tyr Ala Asp Trp Leu Phe
                 85                  90                  95

Thr Thr Pro Leu Leu Leu Leu Asp Leu Ser Leu Leu Ala Gly Ala Asn
                100                 105                 110

Arg Asn Thr Ile Ala Thr Leu Ile Gly Leu Asp Val Phe Met Ile Gly
            115                 120                 125

Thr Gly Ala Ile Ala Ala Leu Ser Ser Thr Pro Gly Thr Arg Ile Ala
130                 135                 140

Trp Trp Ala Ile Ser Thr Gly Ala Leu Leu Ala Leu Leu Tyr Val Leu
145                 150                 155                 160

Val Gly Thr Leu Ser Glu Asn Ala Arg Asn Arg Ala Pro Glu Val Ala
                165                 170                 175

Ser Leu Phe Gly Arg Leu Arg Asn Leu Val Ile Ala Leu Trp Phe Leu
            180                 185                 190

Tyr Pro Val Val Trp Ile Leu Gly Thr Glu Gly Thr Phe Gly Ile Leu
        195                 200                 205

Pro Leu Tyr Trp Glu Thr Ala Ala Phe Met Val Leu Asp Leu Ser Ala
210                 215                 220

Lys Val Gly Phe Gly Val Ile Leu Leu Gln Ser Arg Ser Val Leu Glu
225                 230                 235                 240

Arg Val Ala Thr Pro Thr Ala Ala Pro Thr
                245                 250

<210> SEQ ID NO 4
<211> LENGTH: 273
<212> TYPE: PRT
<213> ORGANISM: Salinibacter ruber

<400> SEQUENCE: 4

Met Leu Gln Glu Leu Pro Thr Leu Thr Pro Gly Gln Tyr Ser Leu Val
 1               5                  10                  15

Phe Asn Met Phe Ser Phe Thr Val Ala Thr Met Thr Ala Ser Phe Val
                20                  25                  30

Phe Phe Val Leu Ala Arg Asn Asn Val Ala Pro Lys Tyr Arg Ile Ser
            35                  40                  45

Met Met Val Ser Ala Leu Val Val Phe Ile Ala Gly Tyr His Tyr Phe
50                  55                  60

Arg Ile Thr Ser Ser Trp Glu Ala Ala Tyr Ala Leu Gln Asn Gly Met
65                  70                  75                  80

Tyr Gln Pro Thr Gly Glu Leu Phe Asn Asp Ala Tyr Arg Tyr Val Asp
                85                  90                  95

Trp Leu Leu Thr Val Pro Leu Leu Thr Val Glu Leu Val Leu Val Met
            100                 105                 110

Gly Leu Pro Lys Asn Glu Arg Gly Pro Leu Ala Ala Lys Leu Gly Phe
        115                 120                 125

Leu Ala Ala Leu Met Ile Val Leu Gly Tyr Pro Gly Glu Val Ser Glu
130                 135                 140

Asn Ala Ala Leu Phe Gly Thr Arg Gly Leu Trp Gly Phe Leu Ser Thr
145                 150                 155                 160

Ile Pro Phe Val Trp Ile Leu Tyr Ile Leu Phe Thr Gln Leu Gly Asp
                165                 170                 175
```

-continued

```
Thr Ile Gln Arg Gln Ser Ser Arg Val Ser Thr Leu Leu Gly Asn Ala
            180                 185                 190
Arg Leu Leu Leu Leu Ala Thr Trp Gly Phe Tyr Pro Ile Ala Tyr Met
        195                 200                 205
Ile Pro Met Ala Phe Pro Glu Ala Phe Pro Ser Asn Thr Pro Gly Thr
    210                 215                 220
Ile Val Ala Leu Gln Val Gly Tyr Thr Ile Ala Asp Val Leu Ala Lys
225                 230                 235                 240
Ala Gly Tyr Gly Val Leu Ile Tyr Asn Ile Ala Lys Ala Lys Ser Glu
                245                 250                 255
Glu Glu Gly Phe Asn Val Ser Glu Met Val Glu Pro Ala Thr Ala Ser
            260                 265                 270
Ala

<210> SEQ ID NO 5
<211> LENGTH: 313
<212> TYPE: PRT
<213> ORGANISM: Leptosphaeria maculans

<400> SEQUENCE: 5

Met Ile Val Asp Gln Phe Glu Glu Val Leu Met Lys Thr Ser Gln Leu
1               5                   10                  15
Phe Pro Leu Pro Thr Ala Thr Gln Ser Ala Gln Pro Thr His Val Ala
            20                  25                  30
Pro Val Pro Thr Val Leu Pro Asp Thr Pro Ile Tyr Glu Thr Val Gly
        35                  40                  45
Asp Ser Gly Ser Lys Thr Leu Trp Val Val Phe Val Leu Met Leu Ile
    50                  55                  60
Ala Ser Ala Ala Phe Thr Ala Leu Ser Trp Lys Ile Pro Val Asn Arg
65                  70                  75                  80

Arg Leu Tyr His Val Ile Thr Thr Ile Ile Thr Leu Thr Ala Ala Leu
                85                  90                  95

Ser Tyr Phe Ala Met Ala Thr Gly His Gly Val Ala Leu Asn Lys Ile
            100                 105                 110

Val Ile Arg Thr Gln His Asp His Val Pro Asp Thr Tyr Glu Thr Val
        115                 120                 125

Tyr Arg Gln Val Tyr Tyr Ala Arg Tyr Ile Asp Trp Ala Ile Thr Thr
    130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
    210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270
```

-continued

```
Phe Gly Ala Trp Leu Leu Val Thr His Ala Asn Leu Arg Glu Ser Asp
        275                 280                 285

Val Glu Leu Asn Gly Phe Trp Ala Asn Gly Leu Asn Arg Glu Gly Ala
        290             295                 300

Ile Arg Ile Gly Glu Asp Asp Gly Ala
305             310
```

OPTICALLY SENSITIVE CELL NETWORK

RELATED APPLICATION

This application claims the benefit of priority under 35 USC 119(e) of U.S. Provisional Patent Application No. 61/582,909 filed Jan. 4, 2012, the contents of which are incorporated herein by reference in their entirety.

FIELD AND BACKGROUND OF THE INVENTION

The present invention, in some embodiments thereof, relates to optics and, more particularly, but not exclusively, to an optically sensitive cell network, a method of producing an optically sensitive cell network, and a method and a system for stimulating an optically sensitive cell network.

The central nervous system (CNS) is the processing center for the nervous system. It receives information from and sends information to the peripheral nervous system. The two main organs of the CNS are the brain and spinal cord. The brain processes and interprets sensory information sent from the spinal cord. Both the brain and spinal cord are protected by three layers of connective tissue called the meninges.

Within the central nervous system is a system of hollow cavities called ventricles. The network of linked cavities in the brain (cerebral ventricles) is continuous with the central canal of the spinal cord. The ventricles are filled with cerebrospinal fluid which is produced by specialized epithelium located within the ventricles called the choroid plexus. Cerebrospinal fluid surrounds, cushions, and protects the brain and spinal cord from trauma. It also assists in the circulation of nutrients to the brain. Neurons are the basic unit of the nervous system. Neurons contain nerve processes which are "finger-like" projections that extend from the nerve cell body. The nerve processes consist of axons and dendrites which are able to conduct and transmit signals. Axons typically carry signals away from the cell body. They are long nerve processes that may branch out to convey signals to various areas. Dendrites typically carry signals toward the cell body. They are usually more numerous, shorter and more branched than axons. Axons and dendrites are bundled together into what are called nerves. These nerves send signals between the brain, spinal cord, and other body organs via nerve impulses. Neurons are classified as either motor, sensory, or interneurons. Motor neurons carry information from the central nervous system to organs, glands, and muscles. Sensory neurons send information to the central nervous system from internal organs or from external stimuli. Interneurons relay signals between motor and sensory neurons.

Various methods are known to stimulate neural tissue. A nerve cell can be stimulated in a number of different ways, including electrical, mechanical, thermal, chemical, and optical. A nerve is a filament of neural tissue composed of cells each having a cell body and one or more axons and dendrites.

A neuron will propagate an electrical impulse after applying a stimulus. The most common form of applying such stimulus is to form a transient current or voltage pulse applied through electrodes. It is recognized that optical energy can also be used to stimulate nerve fibers. One common way of providing light energy is by using a laser. Lasers are characterized by their wavelength and energy level. Classically, lasers have been used in biological applications for tissue ablation. Nevertheless, low power lasers are available for uses other than tissue ablation. The energy required for stimulation large populations of neurons is very small, and the energy required to stimulate an individual neuron is exceedingly small. The strength, duration and frequency of the optical energy can be adjusted to a range acceptable for stimulation of neural tissue.

SUMMARY OF THE INVENTION

According to an aspect of some embodiments of the present invention there is provided a neural network, comprising a plurality of optogenetically modified neural cells being three-dimensionally distributed in a first hydrogel medium and being disconnected from any solid support having a shear modulus above 1 GPa.

According to some embodiments of the invention the first hydrogel medium comprises extracellular matrix (ECM) proteins.

According to an aspect of some embodiments of the present invention there is provided a neural network, comprising a plurality of optogenetically modified neural cells being three-dimensionally distributed in a first hydrogel medium which comprises ECM proteins.

According to some embodiments of the invention the nerve cells are not comprised in a tissue.

According to some embodiments of the invention the cells are distributed in multiple non-overlapping islands of the first hydrogel medium within a second hydrogel medium having a shear modulus which is higher than a shear modulus of the first hydrogel medium, and wherein neural cells of each island are spatially confined by the second hydrogel medium thus forming a sub-network.

According to some embodiments of the invention at least one pair of islands is interconnected by a channel formed in the second hydrogel medium. According to some embodiments of the invention the channel is occupied by at least one axon of a respective at least one neural cell.

According to some embodiments of the invention the channel and the at least one axon are constituted to allow unidirectional flow of axon signals among the pair of islands.

According to an aspect of some embodiments of the present invention there is provided an implantable scaffold, comprising the neural network described herein.

According to some embodiments of the invention the hydrogel medium is adapted for being implanted in the brain of a mammal.

According to an aspect of some embodiments of the present invention there is provided an implantable medical system, comprising the implantable scaffold described herein, and an optical device implantable adjacently to the scaffold and having a light source constituted for optically stimulating the neural cells in vivo.

According to an aspect of some embodiments of the present invention there is provided an implantable medical system, comprising the implantable scaffold described herein, and an electrode system implantable in the scaffold and configured for receiving signals from neural cells responsively to optical stimulation of the neural cells.

According to an aspect of some embodiments of the present invention there is provided a system for stimulating neural cells, comprising a chamber having therein the neural network described herein, and an optical device having a light source constituted for optically stimulating the neural cells while being in the chamber.

According to some embodiments of the invention the chamber is configured to allow stimulating the neural cells from two opposite sides of the chamber.

According to some embodiments of the invention the optical device is configured also for imaging the cells.

According to an aspect of some embodiments of the present invention there is provided a system for drug screening, comprising: a chamber having therein the neural network described herein, a microfluidic system for supplying at least one drug to the cells, and an imaging device constituted for imaging the neural cells while being in the chamber.

According to some embodiments of the invention the chamber is configured to allow imaging the neural cells from two opposite sides of the chamber.

According to some embodiments of the invention the system comprises an electrode system positioned in the neural network and configured for receiving signals from the neural cells responsively to optical stimulation of the neural cells by the optical device.

According to some embodiments of the invention the system the microfluidic system is constituted for supplying different drugs to different regions of the neural network.

According to an aspect of some embodiments of the present invention there is provided a method of treating a neural disorder, comprising implanting in the brain of a subject an implantable scaffold having a neural network, wherein the neural network comprises a plurality of optogenetically modified neural cells being three-dimensionally distributed in a first hydrogel medium and being disconnected from any solid support having a shear modulus above 1 GPa.

According to some embodiments of the invention the method further comprises optically stimulating the neural cells.

According to some embodiments of the invention the method comprises receiving electrical signals from the neural cells responsively to optical stimulation of the neural cells.

According to some embodiments of the invention the method comprises implanting in the brain, adjacently to the scaffold, an optical device having a light source constituted for optically stimulating the neural cells in vivo.

According to some embodiments of the invention the cells are distributed in multiple non-overlapping islands of the first hydrogel medium arranged within a second hydrogel medium having a shear modulus which is higher than a shear modulus of the first hydrogel medium, and wherein neural cells of each island are spatially confined by the second hydrogel medium thus forming a sub-network.

According to some embodiments of the invention the method comprises stimulating at least one of the sub-networks at a spatial resolution compatible with a size of the at least one sub-network.

According to an aspect of some embodiments of the present invention there is provided a method of drug screening, comprising: supplying at least one drug to a neural network having a plurality of optogenetically modified neural cells being three-dimensionally distributed in a first hydrogel medium and being disconnected from any solid support having a shear modulus above 1 GPa; and imaging the neural cells in vitro to determine a response of the cells to the at least one drug.

According to some embodiments of the invention the imaging chamber is configured to allow imaging the neural cells from two opposite sides thereof.

According to some embodiments of the invention the neural cells are neural cells of an individual, and the method is executed for determining responsivity of the individual to the at least one drug.

According to an aspect of some embodiments of the present invention there is provided a method of producing a neural network, comprising: introducing a plurality of neural cells into a first hydrogel medium to form a three-dimensional distribution of the neural cells disconnected from any solid support having a shear modulus above 1 GPa; and optogenetically modifying the neural cells.

According to some embodiments of the invention the method further comprising introducing the first hydrogel medium into a second hydrogel medium having a shear modulus which is higher than a viscosity of the first hydrogel medium, to from islands of the first hydrogel medium within the second hydrogel medium.

According to some embodiments of the invention the method further comprising forming a channel in the second hydrogel medium so as to interconnect a pair of islands by the channel.

According to some embodiments of the invention the method further comprising generating axon guidance conditions within the channel such as to allow at least one axon of the cells to occupy the channel.

According to some embodiments of the invention, forming the channel comprises: forming the channel over a distance selected such that the channel is connected to a first island of the pair but not to a second island of the pair; generating axon guidance conditions within the channel such as to allow at least one axon of cells of the first island to occupy the channel; and extending the channel to interconnect the first island to the second island to allow further growth of the least one axon into the second island.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of a neural network, according to some embodiments of the present invention;

FIG. 2 is a schematic illustration of a neural network, in embodiments of the present invention in which the nerve cells are distributed in multiple non-overlapping islands of a first hydrogel medium within a second hydrogel medium;

FIG. 3 is a schematic illustration of an embodiment of the invention in which one or more pair of islands is interconnected by a channel;

Figure 5:
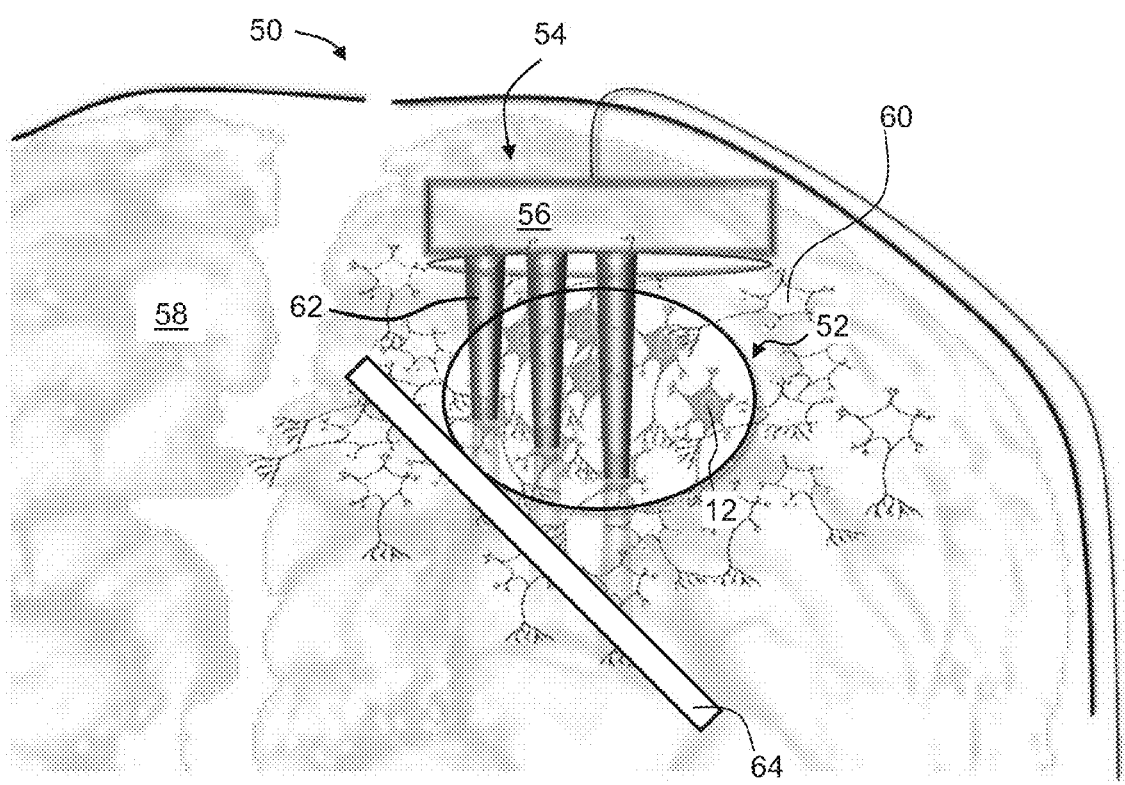
Figure 6A:
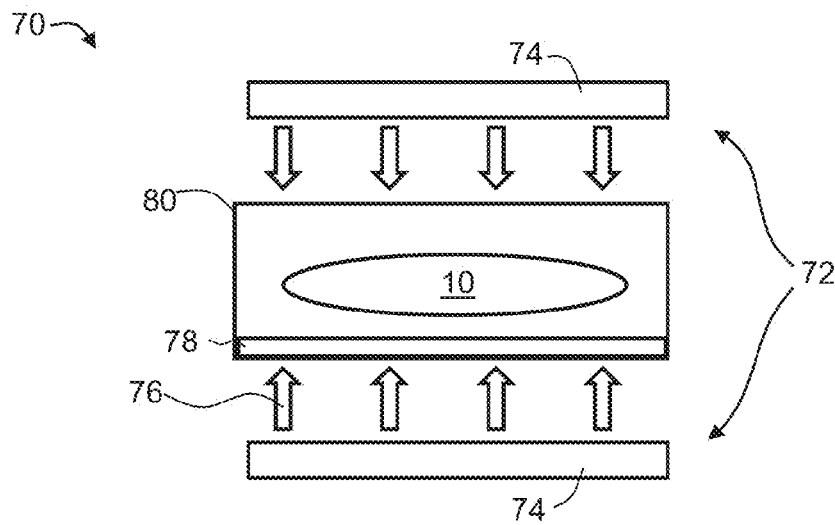
Figure 6B:
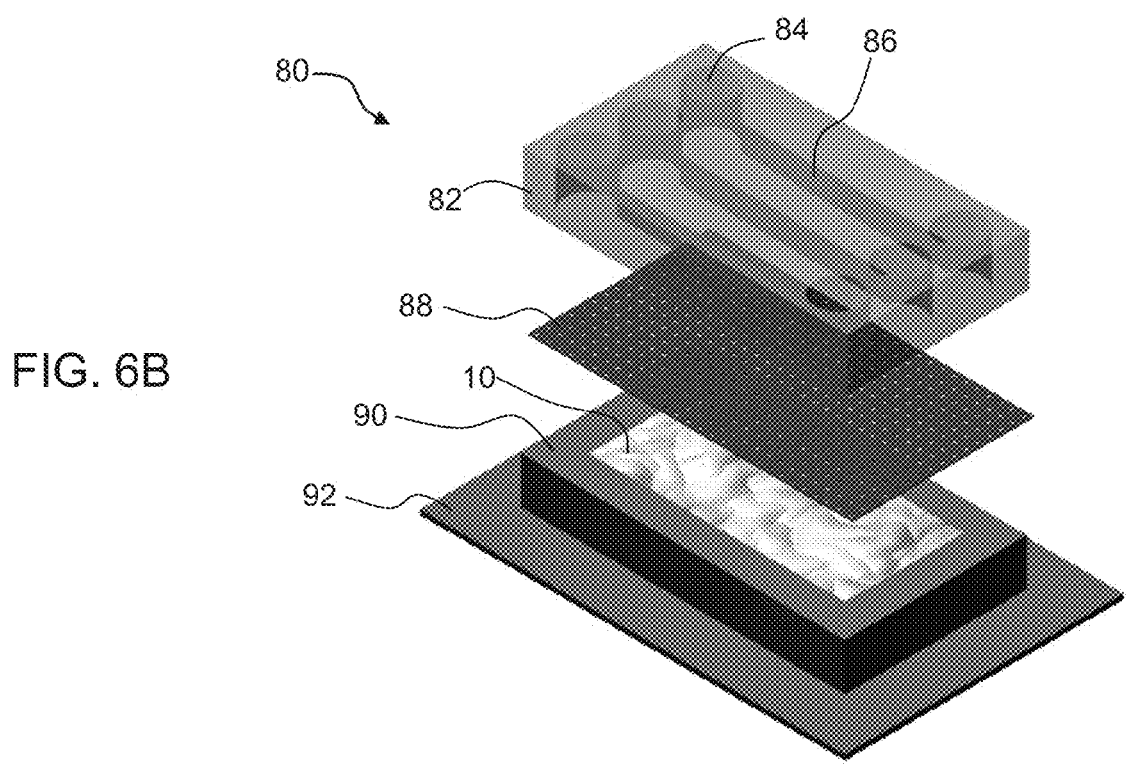
Figure 6C:
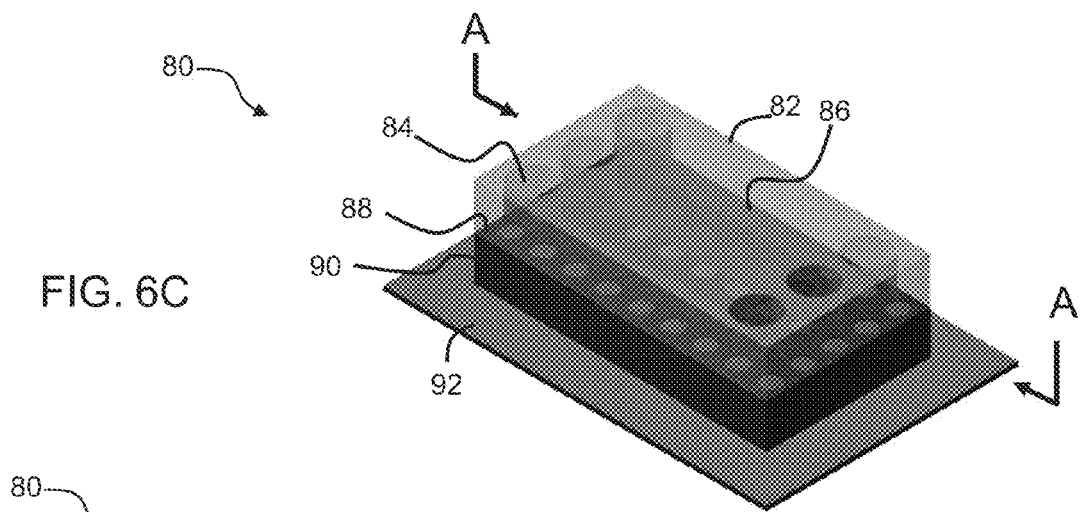
Figure 6D:
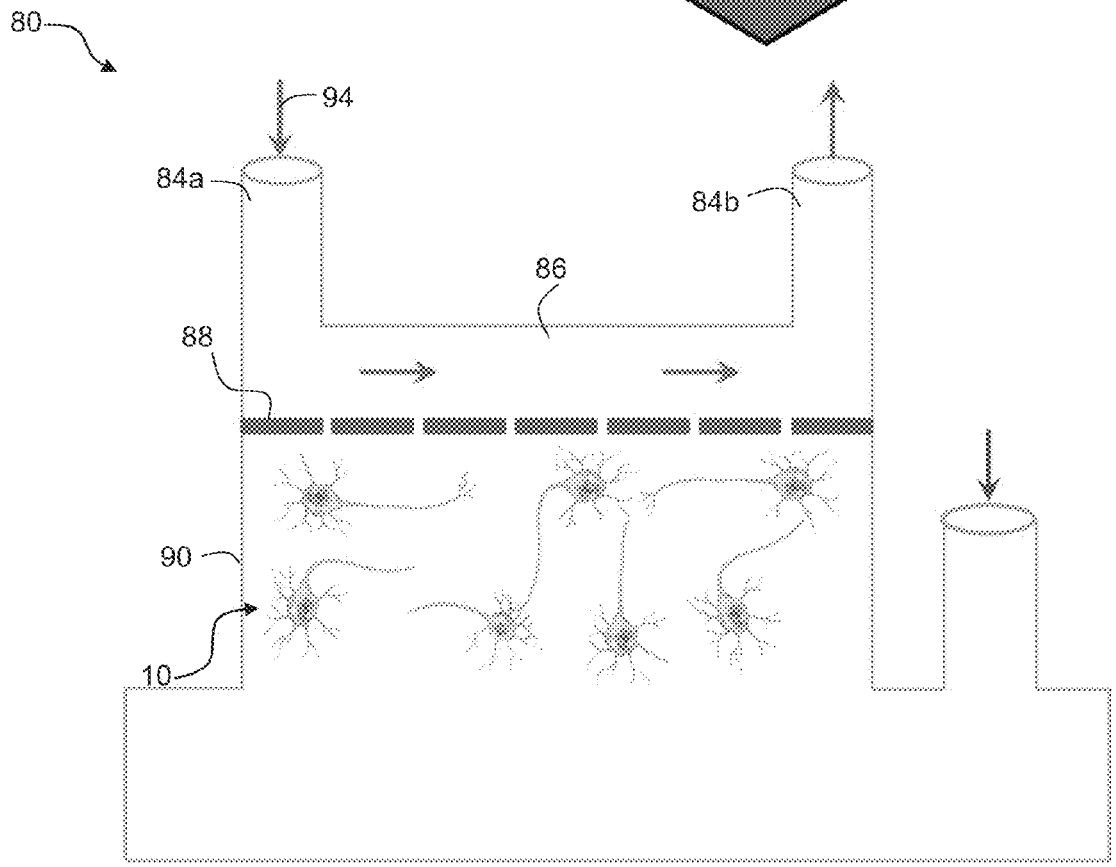
Figure 7A:
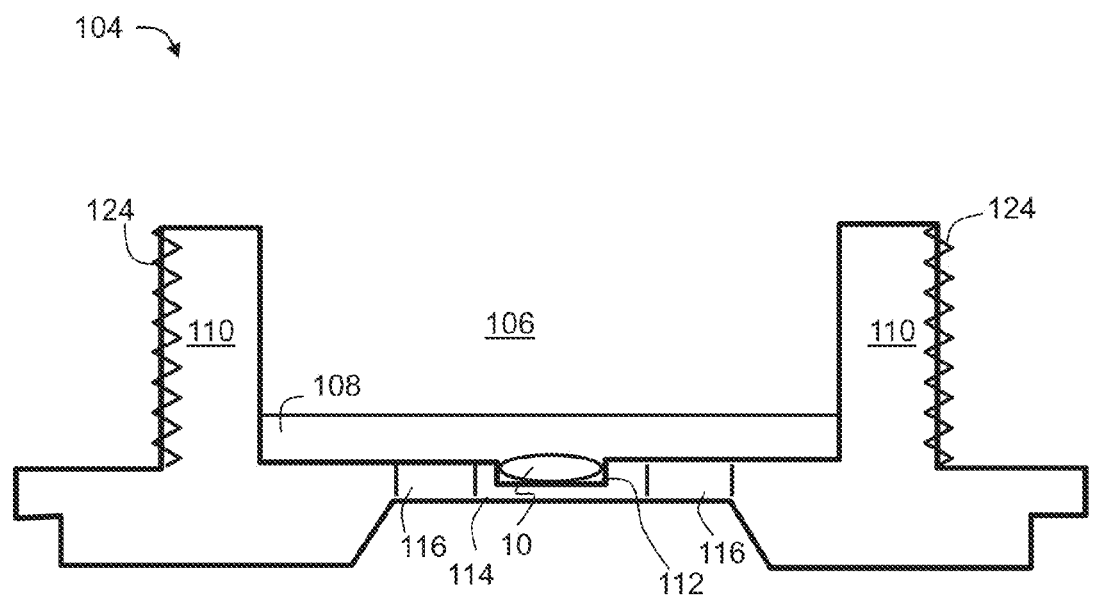
Figure 7B:
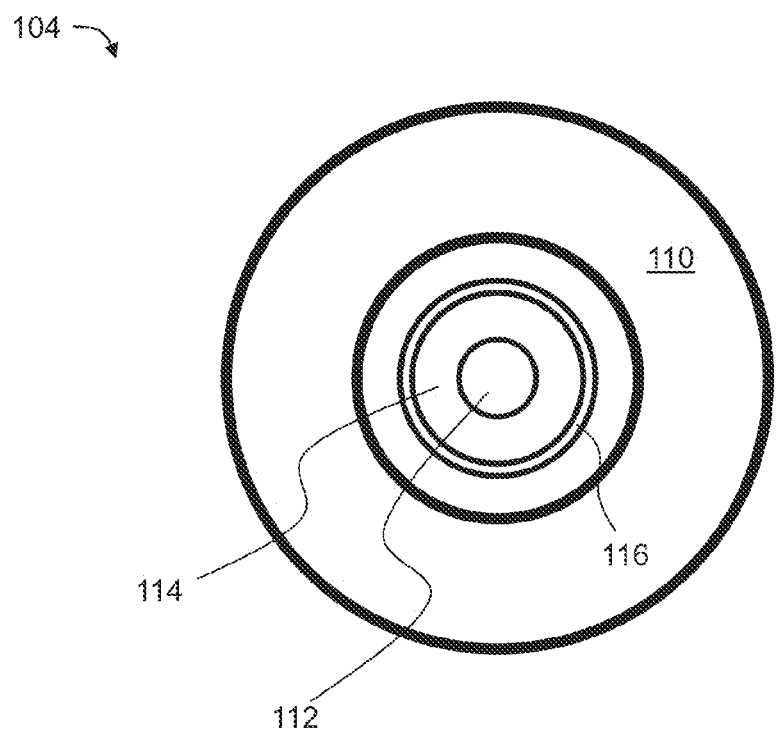
Figure 7C:
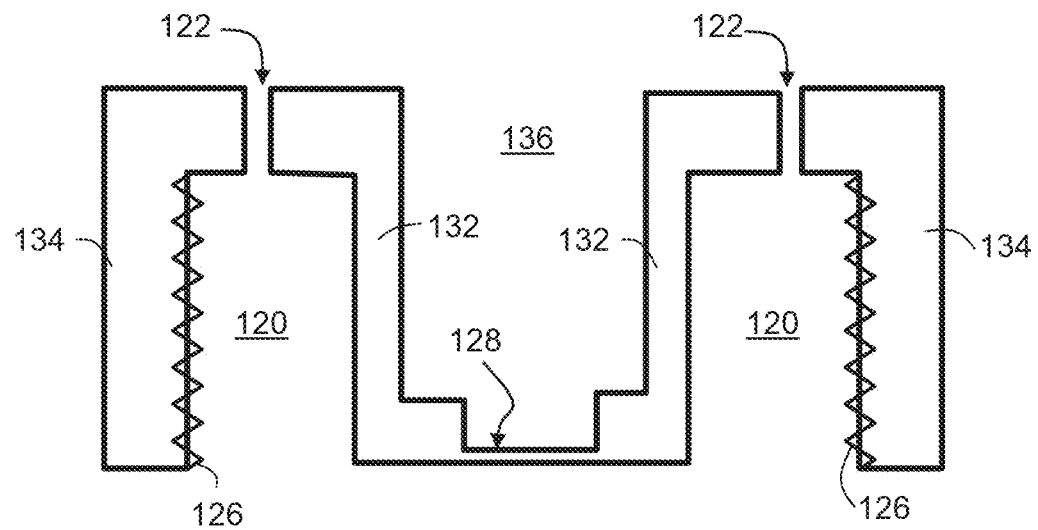
Figure 7D:
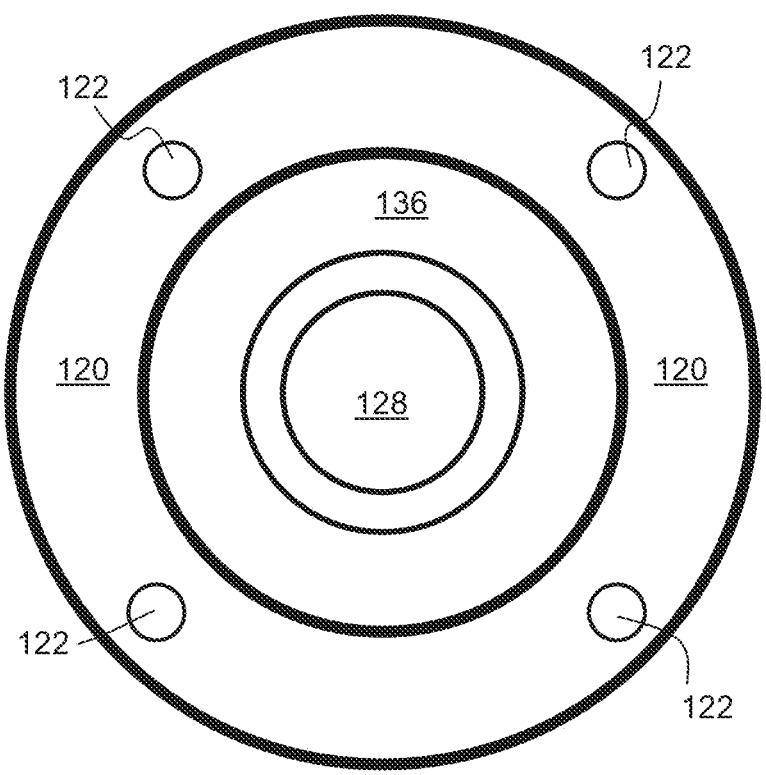
Figure 7E:
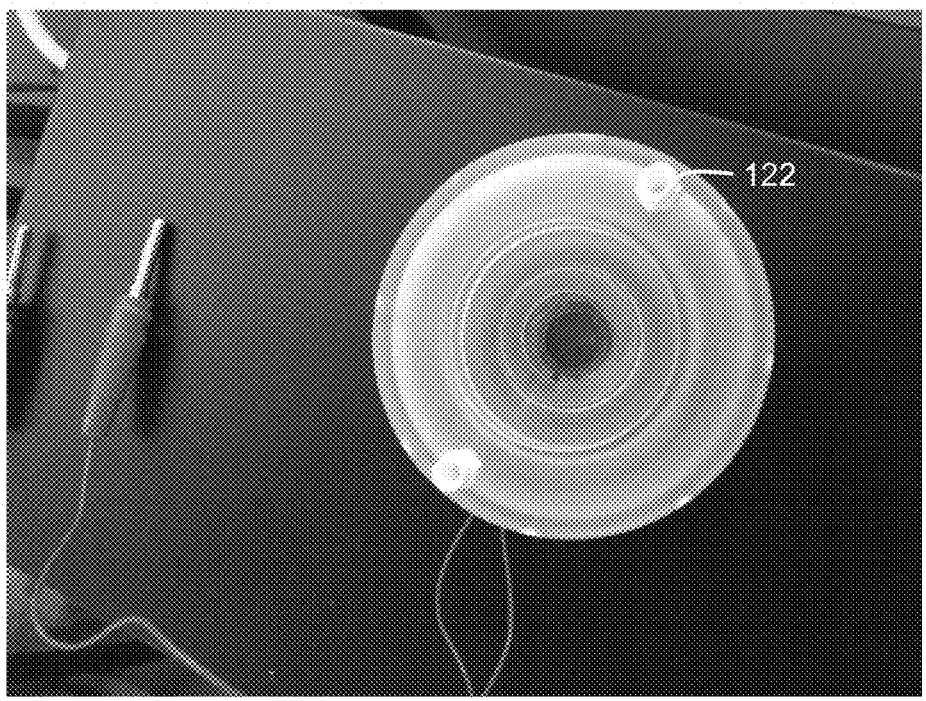
Figure 7F:
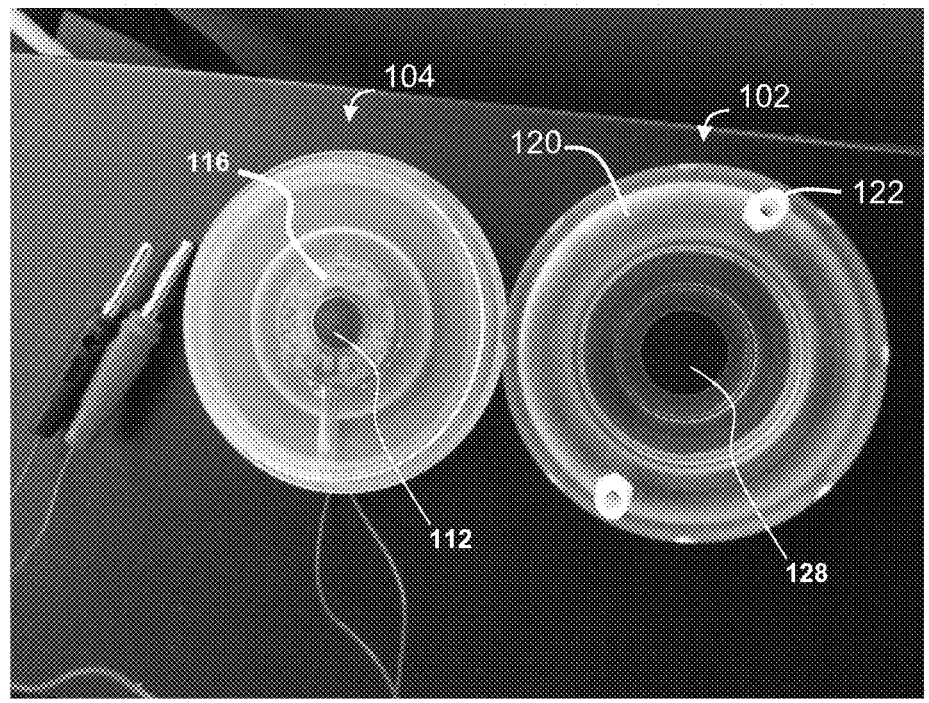
Figure 8:
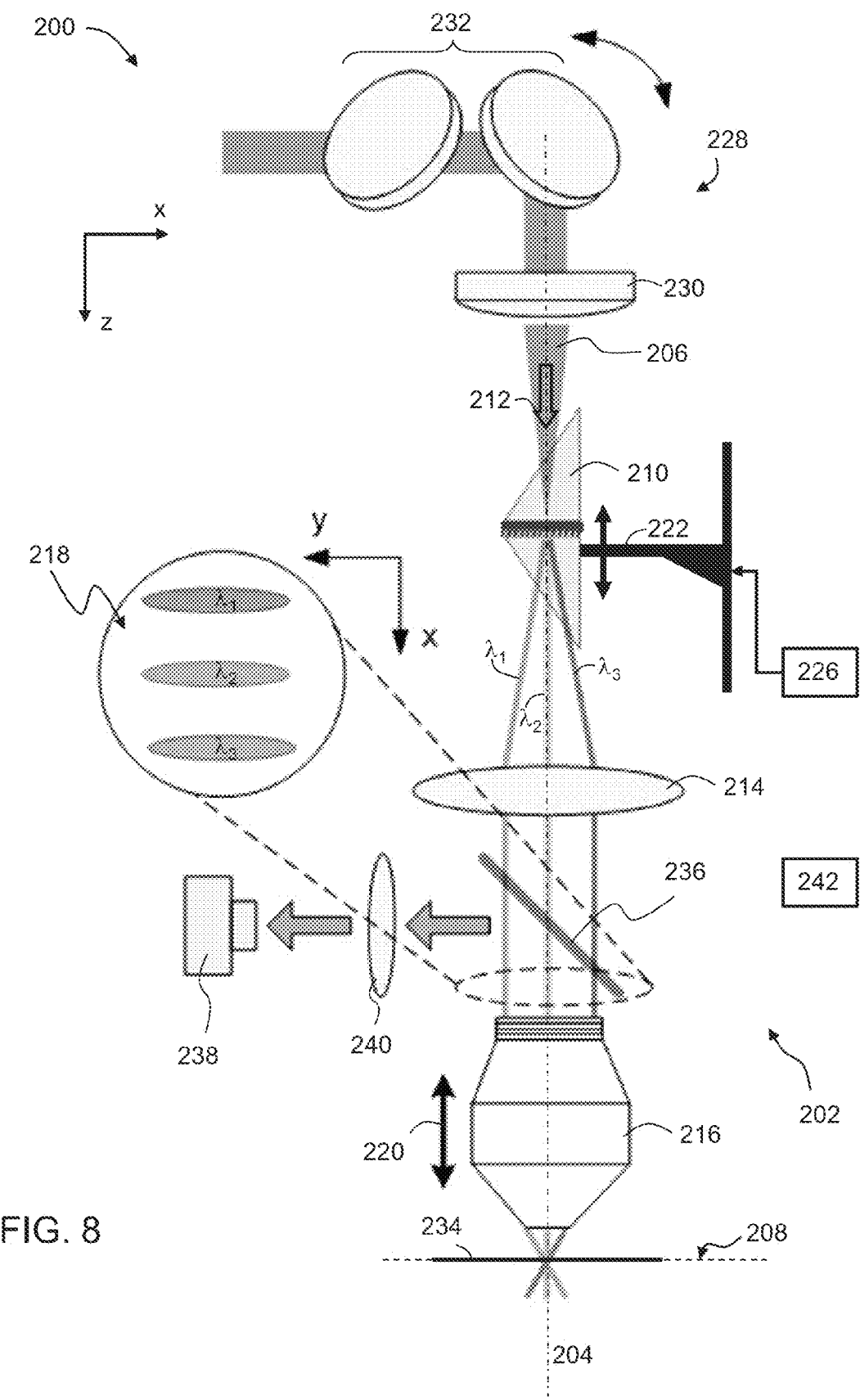
Figure 9:
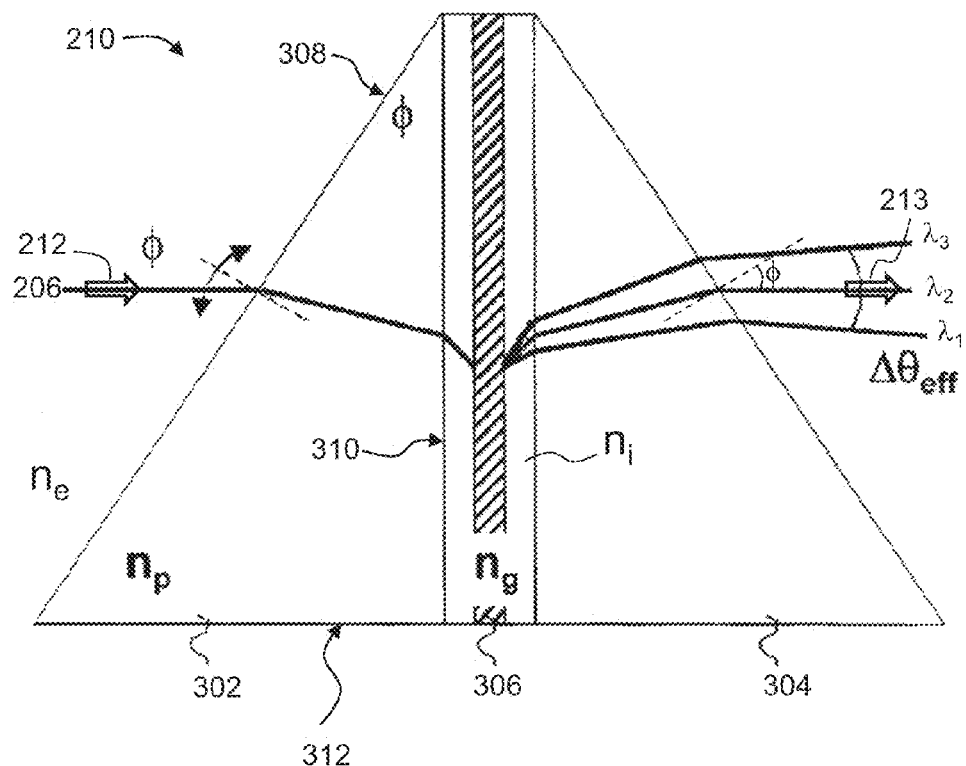
Figure 10:
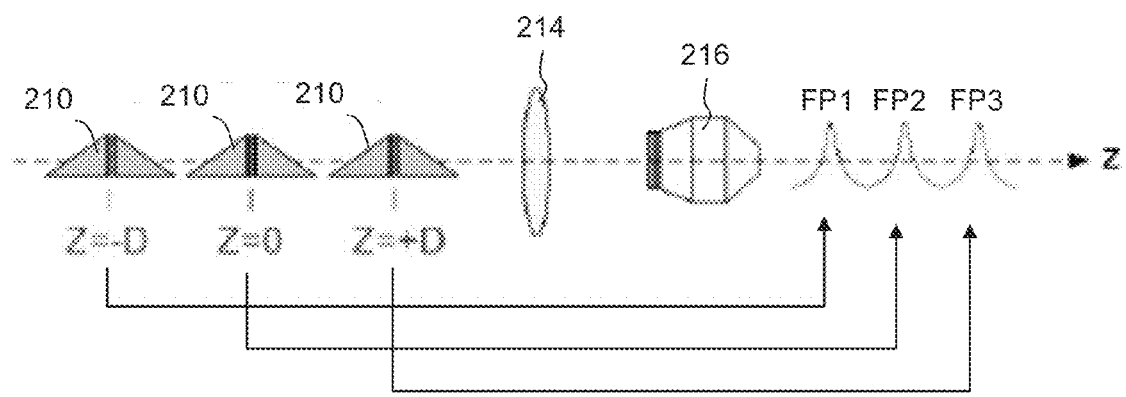
Figure 14A:
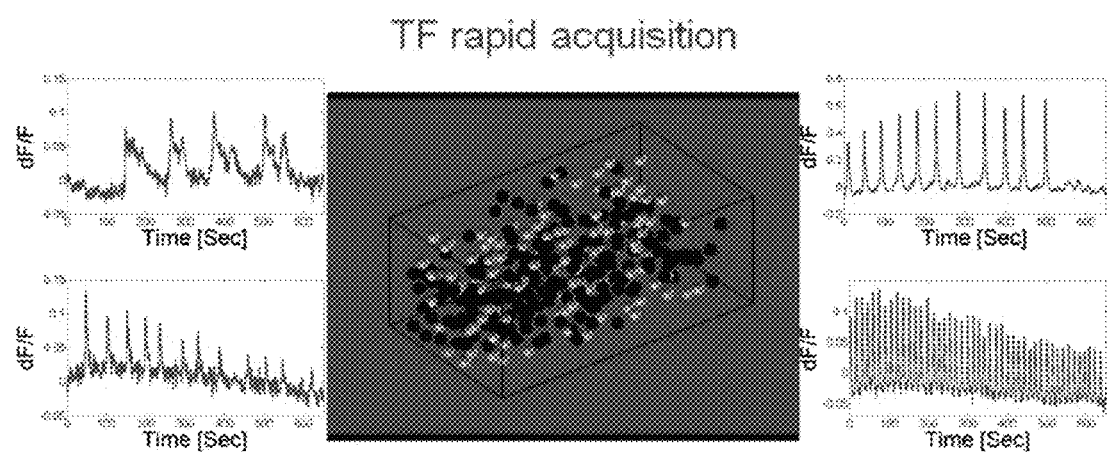
Figure 14B:
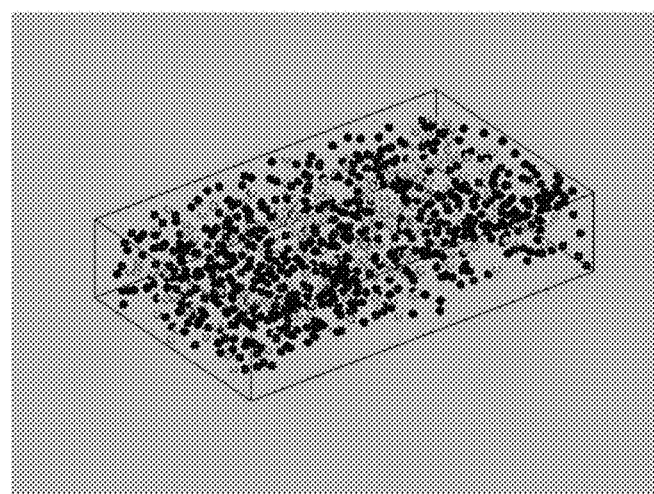
Figure 14C:
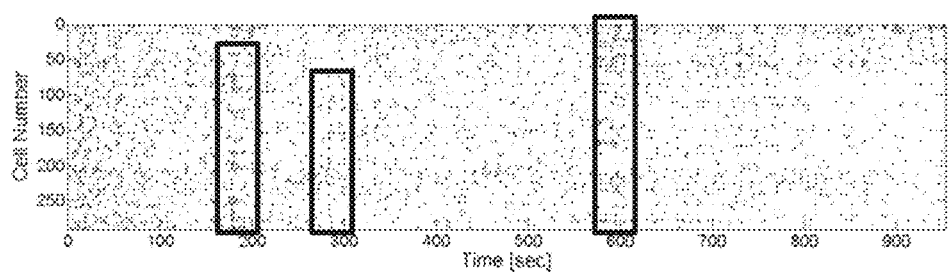
Figure 17:
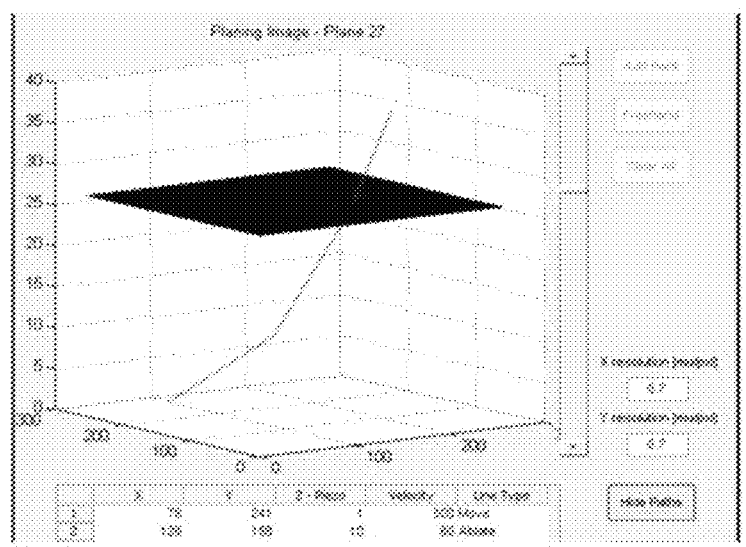
Figure 18:
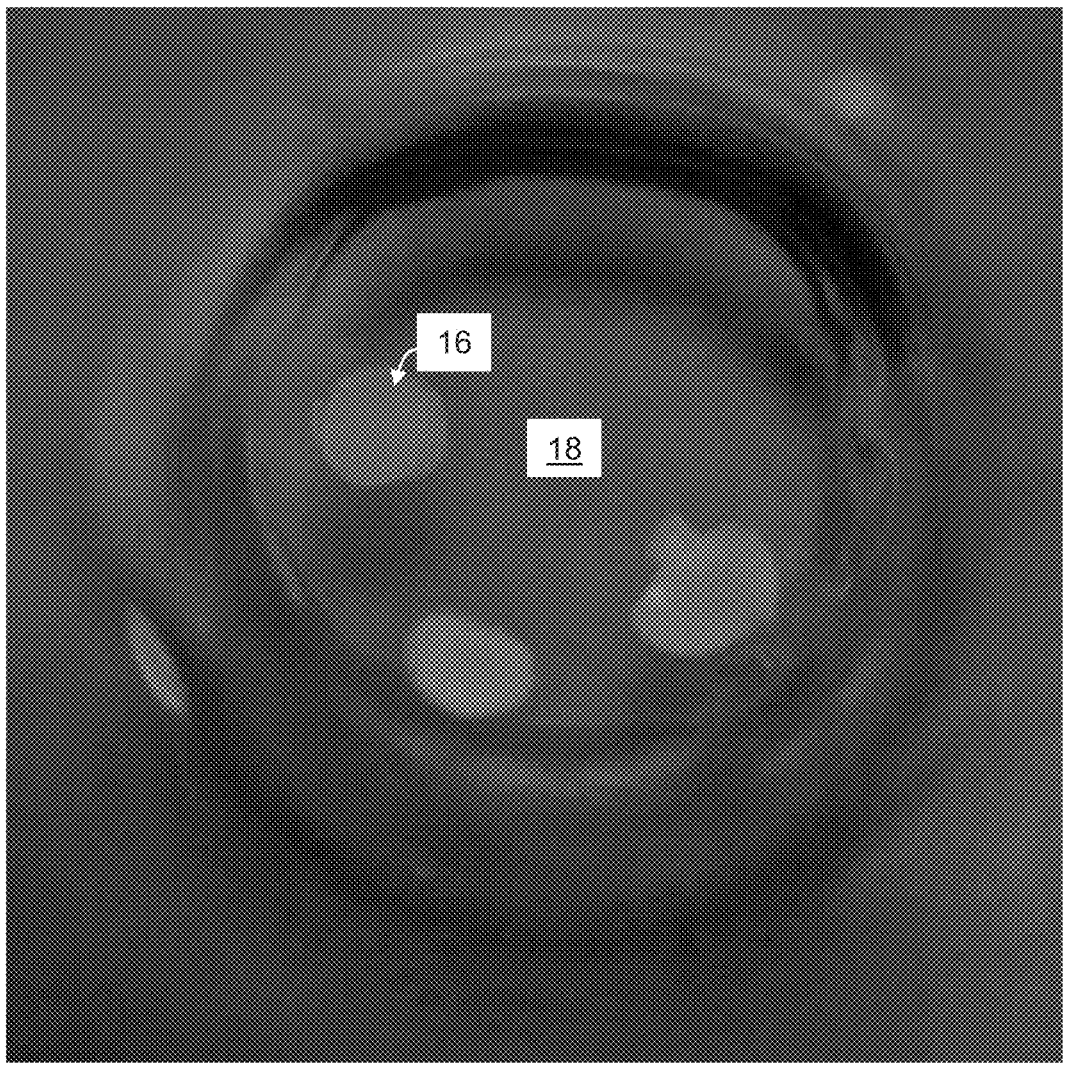
Figure 19:
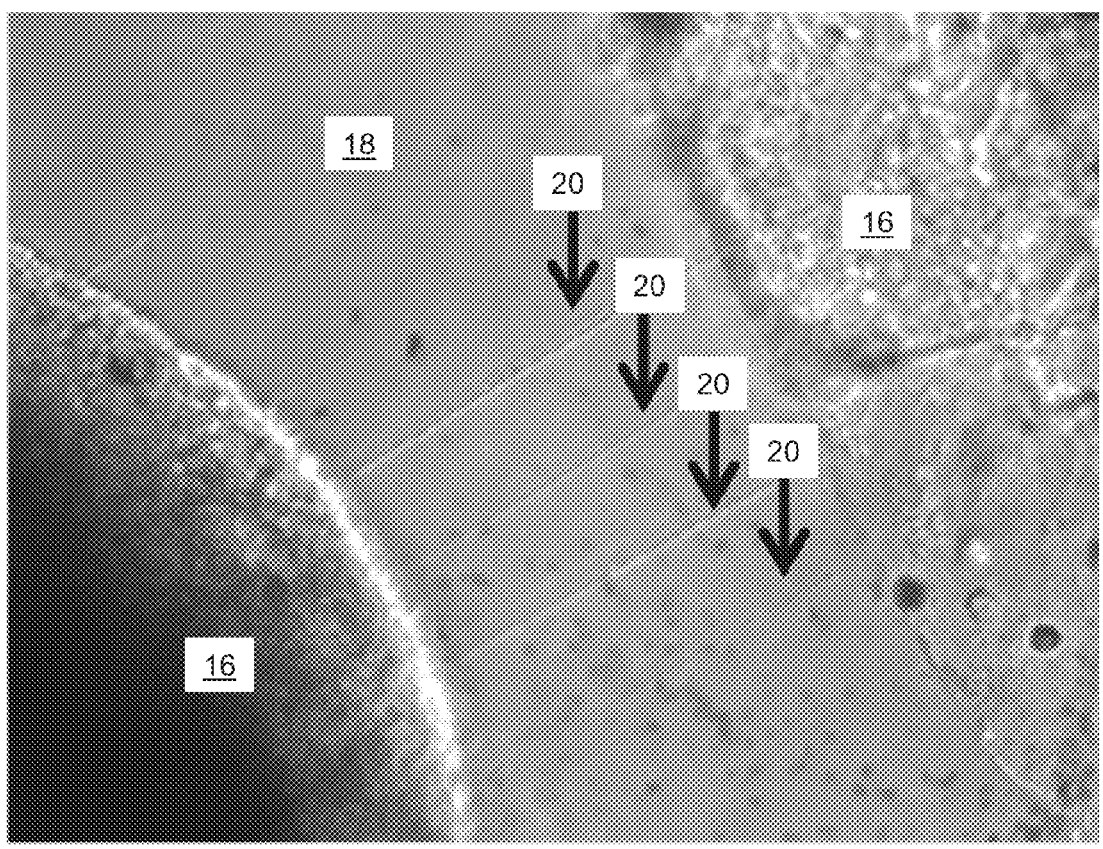
Figure 20:
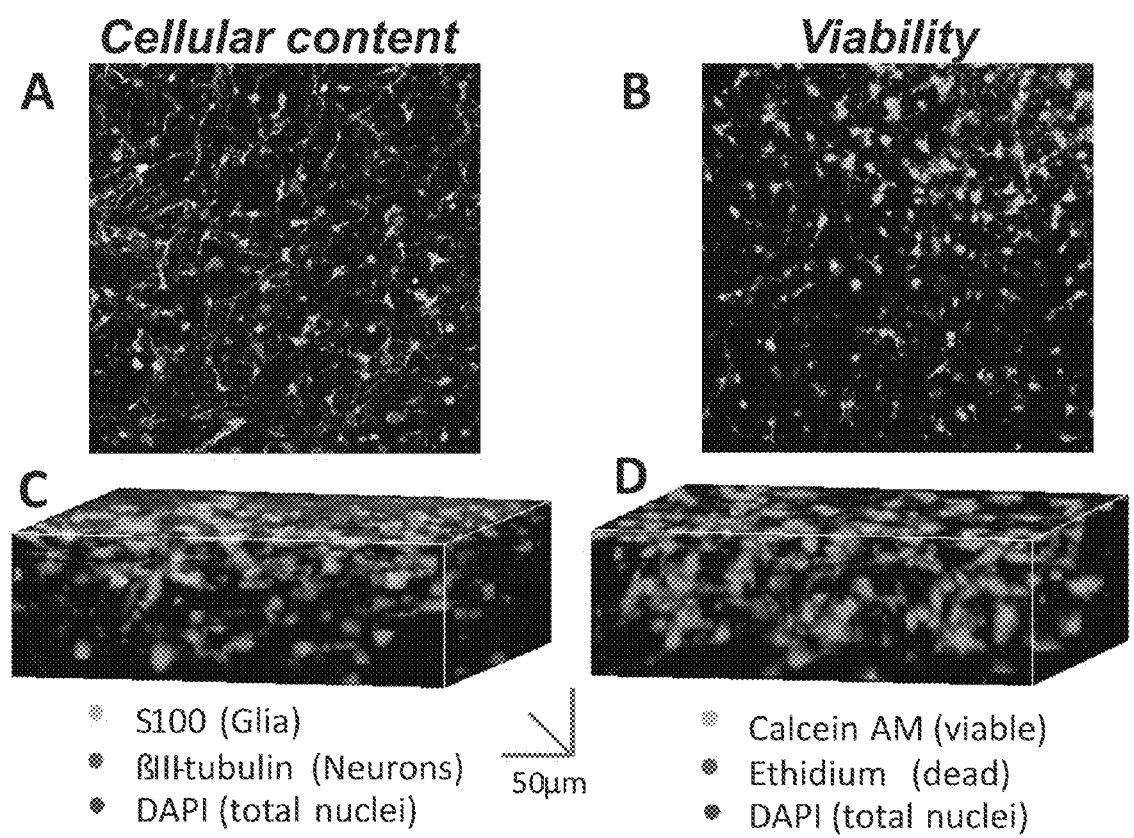
Figure 21:
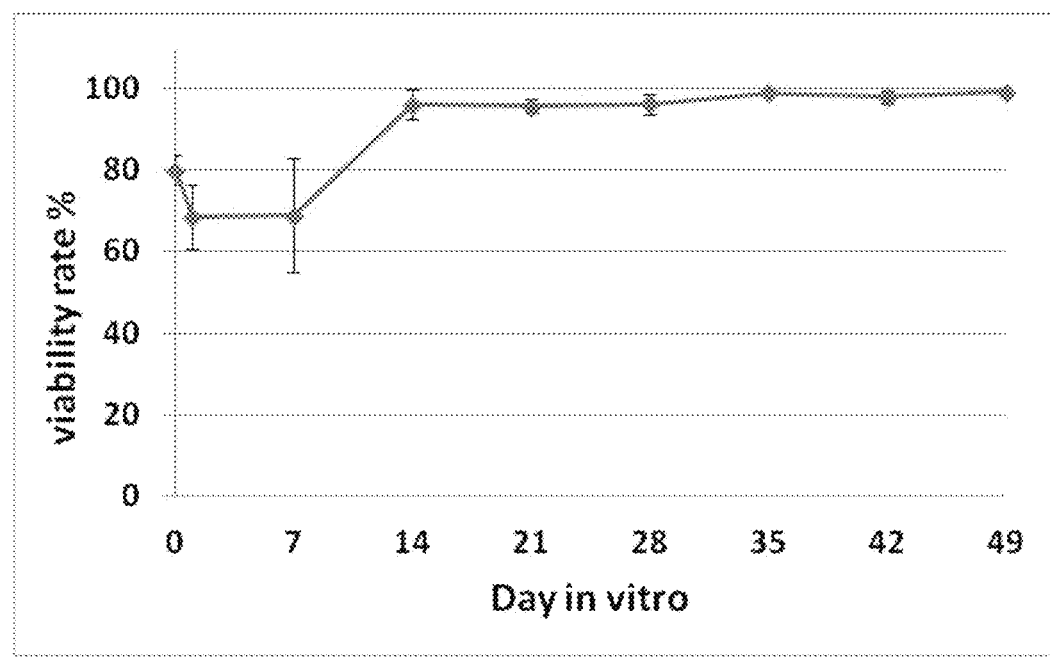

FIGS. 4A-D are schematic illustrations of a representative procedure for forming a channel that ensures a unidirectional flow of axon signals;

FIG. 5 is a schematic illustration of an implantable medical system according to some embodiments of the present invention;

FIG. 6A is a schematic illustration of a system suitable for stimulating nerves, according to some embodiments of the present invention;

FIGS. 6B-D are schematic illustrations of a chamber suitable for use with the system illustrated in FIG. 6A;

FIGS. 7A-D are schematic illustration of an incubation chamber according to some embodiments of the present invention;

FIGS. 7E and 7F are photographs of an incubation chamber according to some embodiments of the present invention;

FIG. 8 is a schematic illustration of a system suitable for stimulating and/or imaging the neural network of the present embodiments;

FIG. 9 is a schematic illustration of a prismatic element according to some embodiments of the present invention;

FIG. 10 is a schematic illustration of an embodiment of the invention according to which the focal plane is controlled by the position of the prismatic element;

FIGS. 11A-F are photographs illustrating the 3D neural networks encapsulated in a hydrogel scaffold. FIGS. 11A, D illustrate neural networks from cortical rat tissue. FIGS. 11B, E illustrate neural networks from cortical dissociated cells from postnatal (B,E) rats. FIGS. 11C, F illustrate neural networks from cortical dissociated cells from embryonic rats. The viability rate of the network in all three models was high, as demonstrated by Calcein staining (FIG. 11A-C) that stains live cells green, and Ethidium homodimer staining (FIG. D-F) that stains the nuclei of dead cells red;

FIGS. 12A-C are photographs illustrating neural networks may be maintained in hydrogels in vitro for up to 65 days. FIG. 12A illustrates calcein staining of neural cells. FIG. 12B illustrates ethidium homodimer staining of neural cells. FIG. 12C illustrates DAPI statining of neural cells;

FIGS. 13A-C are photographs illustrating hydrogel encapsulated neural networks expressing GCaMP3. Changes in fluorescence intensity of the indicator resulting from neuronal spontaneous activity were observed in FIGS. 13A-C;

FIG. 14A illustrates rapid 3D functional microscopy of the neural network. The 3D neural network was stained with organic calcium indicators or transfected with a viral agent for a genetically encoded calcium indicator Fluo-4. Using a temporal focusing based custom made optical system, a 3D volume of 250×500×200 µm [X×Y×Z] in a frame rate of up to 200 frames/sec, which are up to 20 volumes/sec was acquired. A volumetric representation of the cellular content of the 3D network and the fluorescence intensity changes of the indicator was created. The electrically active neurons are represented by white spheres and the non-electrically active cells, mostly glial cells, in black. Four representative patterns of the fluorescence intensity changes in different cells in the scaffold are presented;

FIG. 14B is a pictorial scan following analysis by rapid 3D functional microscopy. The size of the scaffold was: 600× 1000×200 µm [X×Y×Z]. Imaging rate: up to 200 frames/sec (20 volumes/sec); ×10 objective lens. The scan shows of the 966 cells that were comprised in the scaffold, 290 of them were active (white);

FIG. 14C is a raster plot of the scan illustrated in FIG. 14B which shows that the activity of the neural network is not synchronized;

FIGS. 15A-D illustrate that neural cells may be genetically modified to express the light gated channel, Channelrhodopsin2 (ChR2) in 2D culture (on a multielectrode array—FIGS. 15A, B) and 3D culture—(in a Matrigel scaffold)—FIG. 15C. FIG. 15D illustrates a model of a 3D optical stimulation system using holography according to embodiments of the present invention;

FIGS. 16A-B illustrate ablation of the hydrogel according to embodiments of the present invention. A MatLab based application allows the planning and the accurate automatic execution of a 2D (FIG. 16A) ablation pattern. FIG. 16B demonstrates the directed growth of postnatal cortical tissue originated from rat and encapsulated in a hydrogel scaffold, into the designed ablation pattern;

FIG. 17 illustrates ablation of the hydrogel according to embodiments of the present invention. A MatLab based application allows the planning and the accurate automatic execution of any 3D ablation pattern;

FIG. 18 is a photograph of a neural network, in embodiments of the present invention in which the nerve cells are distributed in multiple non-overlapping islands of a first hydrogel medium within a second hydrogel medium;

FIG. 19 is a light microscope image (×20 objective) of a neural network, in embodiments of the invention in which one or more pair of islands is interconnected by a channel;

FIGS. 20A-D are images of rat cortical dissociated cells encapsulated in a Matrigel scaffold. The cells were stained by whole gel immunostaining using antibodies that recognize glial cells and neuronal cells. Nuclei were stained with Dapi (A and C). The viability rate of the network was determined using a whole-gel staining using Calcein AM and ethidium and nuclei were stained with Dapi (B and D). Images were captured using confocal microscopy (A,B) and stack representation of 120 µm stack (C,D) were created using ImageJ software; and FIG. 21 is a graph illustrating that the neural networks can survive in a hydrogel for up to 49 days in vitro.

DESCRIPTION OF SPECIFIC EMBODIMENTS OF THE INVENTION

The present invention, in some embodiments thereof, relates to optics and, more particularly, but not exclusively, to an optically sensitive cell network, a method of producing an optically sensitive cell network, and a method and a system for stimulating an optically sensitive cell network.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
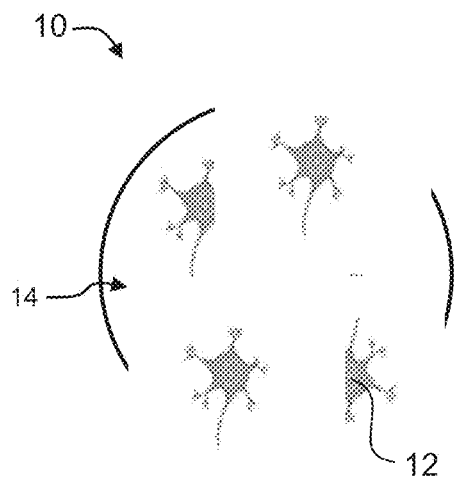

Referring now to the drawings, FIG. 1 is a schematic illustration of a neural network 10, according to some embodiments of the present invention. Neural network 10 comprises a plurality of optogenetically modified neural cells 12.

The term "neural cells" (also referred to herein as "neurons") refers to electrically excitable biological cells that process and transmit information through electrical and chemical signals.

The neural cells which make up the neuronal networks described herein are preferably mammalian neural cells, e.g., human. The neural cells may be derived from adult tissue, embryonic tissue or postnatal tissue.

Preferably, the neural cells are those which are naturally found in the brain. Examples of neural cells include, but are not limited to Basket cells, interneurons that form a dense plexus of terminals around the soma of target cells, found in the cortex and cerebellum; Betz cells, large motor neurons; Medium spiny neurons, most neurons in the corpus striatum; Purkinje cells, huge neurons in the cerebellum, a type of Golgi I multipolar neuron; Pyramidal cells, neurons with triangular soma, a type of Golgi I; Renshaw cells, neurons with both ends linked to alpha motor neurons and Granule cells, a type of Golgi II neuron.

According to a particular embodiment, the neurons are cortical neurons.

The neurons of the present embodiments may be afferent neurons, efferent neurons or interneurons.

The neurons may be a primary culture of neurons, taken directly from a particular subject during a biopsy, or may be from a cell line. In order to obtain a sufficient quantity of neurons they may be expanded in vitro.

According to a particular embodiment, the neuronal cells are differentiated ex vivo from stem cells including embryonic stem cells, mesenchymal stem cells, neural stem cells or induced pluripotent stem cells (iPSCs).

It will be appreciated that when the neural cells are derived from a primary culture or from a subject, the neural cell population may also comprise additional cells which are natively found in the brain. Such cells include and endothelial cells, fibroblasts and glial cells (e.g. oligodendrocytes). Thus, both homogenous cell populations and heterogeneous cell populations (mixed cell populations) are contemplated for some embodiments of this invention.

Culturing conditions for neuronal cells are known in the art. Typically, the cells are cultured in a medium that supports nerve growth—for example Minimal Essential Media (MEM, Sigma). The medium may comprise additional components such as serum, insulin and antibiotics. In addition, the medium may comprises additional components that support neural growth (e.g. growth factors) examples of which include but are not limited to nerve growth factor (NGF) and brain derived nerve factor containing (BDNF). An exemplary medium for culturing neural cells is MEM supplemented with 100 μl/ml of NU Serum (BD Biosciences), 30 mg/ml of L-Glutamine (Sigma), 1:500 B-27 supplement (Gibco), 50 ng/ml of Nerve Growth Factor (NGF, Alomone labs), 10 ng/ml of Brain-Derived Neurotrophic Factor (BDNF, R&D systems), 25 μg/ml of Insulin (Sigma), and 2 μg/ml of Gentamicin.

A "neural network" as described herein, refers to a plurality of interconnected neurons (i.e. at least two neurons) whose activation defines a recognizable linear pathway. The interface through which neurons interact with their neighbors usually consists of several axon terminals connected via synapses to dendrites on other neurons. If the sum of the input signals into one neuron surpasses a certain threshold, the neuron sends an action potential (AP) at the axon hillock and transmits this electrical signal along the axon.

As used herein "optogenetically modified neural cells" refers to neural cells which have been genetically modified to express a light sensitive protein (e.g., ion channel) which allows the neural cell to fire an action potential in response to stimulation with light.

The present embodiments contemplates expression of ion channels which may be activated or inhibited by light of particular wavelengths—including bacteriorhodopsins (SEQ ID NO: 2), proteorhodopsins (e.g. SEQ ID NO: 1), channelrhodopsins, deltarhodopsin (e.g. SEQ ID NO: 3), xanthorhodosin (e.g. SEQ ID NO: 4), opsin (SEQ ID NO: 5) and halorhodopsins. Examples of such ion channels are disclosed in Sjulson et al, 2008, Chem. Rev. May; 108(5):1588-602 the contents of which are incorporated herein by reference. An exemplary channel which enables neural excitation is Channelrhodopsin-2 (ChR2), see for example Bi et al, 2006 Neuron. April 6; 50(1):23-33. An exemplary channel which enables neural inhibition is NpHR, see for example Zhang et al., 2007 Nature. April 5; 446(7136):633-9.

Other exemplary ion channels are described in Fenno L, Yizhar O, Deisseroth K. The development and application of optogenetics. Annu Rev Neurosci. 2011; 34:389-412. doi: 10.1146/annurev-neuro-061010-113817, the contents of which are incorporated herein by reference. Additional light sensitive ion channels are described in U.S. Patent Application No. 20110224145, the contents of which are incorporated herein by reference.

In order to obtain an optogenetically modified neural cell, the cell is transfected with an exogenous polynucleotide sequence designed and constructed to express at least a functional portion of the light sensitive ion channel. Accordingly, the exogenous polynucleotide sequence may be a DNA or RNA sequence encoding a light sensitive ion channel molecule, capable of producing an action potential in the cell.

According to one embodiment, the neural cells are genetically modified prior to encapsulation in the hydrogel. According to another embodiment, the neural cells are genetically modified following encapsulation in the hydrogel.

To express exogenous light sensitive ion channels in neuronal cells, a polynucleotide sequence encoding same is preferably ligated into a nucleic acid construct suitable for mammalian cell expression. Such a nucleic acid construct includes a promoter sequence for directing transcription of the polynucleotide sequence in the cell in a constitutive or inducible manner.

It will be appreciated that the nucleic acid construct of some embodiments of the invention can also utilize homologues which exhibit the desired activity (i.e., ability to produce action potentials in response to light). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to known genbank sequences, as determined using the BestFit software of the Wisconsin sequence analysis package, utilizing the Smith and Waterman algorithm, where gap weight equals 50, length weight equals 3, average match equals 10 and average mismatch equals −9.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for example the tetracycline-inducible promoter (Zabala M, et al., Cancer Res. 2004, 64(8): 2799-804).

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vector may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include neuron-specific promoters such as the neurofilament promoter [Byrne et al. (1989) Proc. Natl. Acad. Sci. USA 86:5473-5477], Thy1 (Thy1 cell surface antigen), CamKII and synapsin.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding the light sensitive ion channel can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, neural cells can be infected with Adeno-associated virus (AAV) or Lentivirus.

Recombinant viral vectors are useful for in vivo expression of the light sensitive ion channels since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation, optical transfection by focused laser beam and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses. Additionally, viral infection is advantageous since the cells can be transfected also after the encapsulation of the cells in the hydrogel scaffold at any stage of culturing.

Currently preferred in vivo nucleic acid transfer techniques include transfection with viral or non-viral constructs, such as adenovirus, lentivirus, Herpes simplex I virus, or adeno-associated virus (AAV) and lipid-based systems.

Exemplary AAV viral vectors that may be used to generate the optogenetically modified neural cells of the present embodiments are provided in Table 1, herein below.

TABLE 1

| Catalog # | Vector Name | Map/Sequence |
|---|---|---|
| AV-1-PV2478 | AAV2/1.hSynap.GCaMP5G(GCaMP3-T302L.R303P.D380Y).WPRE.SV40 | Penn Vector P2478 |
| AV-9-PV2478 | AAV2/9.hSynap.GCaMP5G(GCaMP3-T302L.R303P.D380Y).WPRE.SV40 | Penn Vector P2478 |
| AV-1-PV1627 | AAV2/1.hSynap.GCaMP3.WPRE.SV40 | Penn Vector P1627 |
| AV-9-PV1627 | AAV2/9.hSynap.GCaMP3.WPRE.SV40 | Penn Vector P1627 |
| AV-1-PV2368 | AAV2/1.CMV.rSynGCaMP3.SV40 | PennVector P2368 |
| AV-1-20938M | AAV2/1.CAG.hChR2(H134R)-mCherry.WPRE.SV40 | Addgene 20938 MOD |
| AV-9-20938M | AAV2/9.CAG.hChR2(H134R)-mCherry.WPRE.SV40 | Addgene 20938 MOD |
| AV-1-20071P | AAV2/1.CAG.ChR2-Venus.W.SV40 | Addgene 20071 |
| AV-9-20071P | AAV2/9.CAG.ChR2-Venus.W.SV40 | Addgene 20071 |
| AV-1-PV2822 | AAV1.Syn.GCaMP6f.WPRE.SV40 | |
| AV-1-PV2823 | AAV1.Syn.GCaMP6m.WPRE.SV40 | |
| AV-1-PV2833 | AAV1.CAG.GCaMP6s.WPRE.SV40 | |
| AV-1-26972P | AAV2/1.hSyn.eNpHR3.0-EYFP.WPRE.hGH | Addgene 26972 |
| AV-9-26972P | AAV2/9.hSyn.eNpHR3.0-EYFP.WPRE.hGH | Addgene 26972 |
| AV-1-26971P | AAV2/1.CamKIIa.eNpHR3.0-EYFP.WPRE.hGH | Addgene 26971 |
| AV-9-26971P | AAV2/9.CamKIIa.eNpHR3.0-EYFP.WPRE.hGH | Addgene 26971 |

Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

The present embodiments further contemplate modifying the neural cells to express a detectable moiety including for example a calcium indicator (GCaMP3/5/6) or a voltage-sensitive fluorescent protein (VSFP2). The detectable signal may be expressed as a fusion protein such that it is localized to a specific subcellular compartment. For example, syn-GCaMP is GCaMP3 fused with Synaptophysin that localizes the calcium indicator to synaptic vesicles and act as a reporter of synaptic activity—see for example Fenno et al., Annu Rev Neurosci, 2011:34; 389-412.

Various types of detectable or reporter moieties may be conjugated to the light sensitive ion channel of embodiments of the invention. These include, but not are limited to, a radioactive isotope (such as [125]iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomography (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Tracers and cell probes may also be used to label the neuronal cells of the present invention. Such tracers include for example lipophilic dyes, carbocyanine dyes (e.g. diI, diS and diO), arbocyanine dyes, dextran conjugates, cell stains such as 1,1'-Didodecyl-3,3,3',3'-Tetramethylindocarbocyanine Perchlorate ($DiIC_{12}(3)$), 1,1'-Dihexadecyl-3,3,3',3'-Tetramethylindocarbocyanine Perchlorate ($DiIC_{16}(3)$), 1,1'-Dilinoleyl-3,3,3',3'-Tetramethylindocarbocyanine Perchlorate (FAST DiI™ oil; $DiI\Delta^{9,12}\text{-}C_{18}(3)$, $ClO_4$), 1,1'-Dilinoleyl-3,3,3',3'-Tetramethylindocarbocyanine, 4-Chlorobenzenesulfonate (FAST DiI™ solid; $DiI\Delta^{9,12}\text{-}C_{18}(3)$, CBS) and 1,1'-Dioctadecyl-3,3,3',3'-Tetramethylindocarbocyanine Perchlorate ('DiI'; $DiIC_{18}(3)$) and Acetoxymethyl (AM) esters. Such tracers and cell probes are widely available—for example from Invitrogen or Sigma.

Additional tracers and dyes which distinguish between live and dead cells, cell nucleus and cell cytoplasm are also contemplated. Further cells which selectively stain additional subcellular compartments (e.g. mitochondria, cell membrane) are also contemplated.

Before providing a further detailed description of the neural network according to some embodiments of the present invention, attention will be given to the potential applications offered thereby.

Neural network 10 can be used in many applications. For example, in some embodiments of the present invention neural network 10 serves as or is incorporated in an implantable scaffold, adapted for being implanted in the brain of a mammal. Once implanted, neural cells 12 of network 10 integrate and form neuronal connections with the neurons of the host brain.

In some embodiments of the present invention neural network 10 is incorporated in an implantable medical system which comprises an implantable scaffold including neural network 10, and an optical stimulation device implantable adjacently to scaffold and having a light source constituted for optically stimulating neural cells in vivo.

In some embodiments of the present invention neural network 10 is incorporated in a system for stimulating nerves in vitro. Such system can include a chamber having therein neural network 10, and an optical device configured for imaging and/or optically stimulating neural cells while being in the chamber. This system can be used in the field of biological, chemical and pharmacological research wherein the response of the neural cells for stimulation under various biological, chemical and/or pharmacological conditions can be investigated. In particular, such system can be used for neuron-based screening of targeted drugs. In some embodiments of the present invention, network 10 comprises neural cells of a specific subject, and the system is employed for subject-specific drug screening.

Referring again to FIG. 1, cells 12 are optionally and preferably distributed three-dimensionally in a hydrogel medium generally shown at 14. The distribution of cells 12 in medium 14 is three-dimensional in the since that there are at least four or at least 10 or at least 100 cells which do not engage the same plane. Optionally and preferably one or more of the cells by itself is non-planar. For example, the soma can engage a plane, while the dendrites and axon can lie outside this plane. Thus the neurons are not simply attached to the surface of the hydrogel, but at least a portion thereof, more preferably all the neurons are embedded within the hydrogel.

As used herein, "hydrogel medium" refers to a hydrophilic polymer that imbibes water to form a hydrated polymer system in an equilibrium state such that at least 10% or at least 20% or at least 30% or at least 40% or at least 50% of the hydrated polymer system is composed of water. In some embodiments, hydrogels according to the present disclosure can contain greater than about 70-90 volume % water.

Typically, the shear modulus of hydrogel medium 14 is from about 15 Pa to about 500 Pa, more preferably from about 15 Pa to about 200 Pa.

Typically, the hydrogel is selected such that it allows the passage of light so as to allow optical stimulation and activation of light sensitive ion channels in the neural cells. According to some embodiments, the hydrogel is substantially transparent.

Nonlimiting suitable materials which may be used to form hydrogels include synthetic polymers such as polyalkylene oxides including poly(ethylene glycol), poly(ethylene oxide), and poly(ethylene oxide)-co-poly(propylene oxide) block copolymers (poloxamers and meroxapols), partially or fully hydrolyzed polyvinyl alcohol), poly(vinylpyrrolidone), poly(ethyloxazoline), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as FICOLL™, polysucrose, hyaluronic acid, dextran, heparan sulfate, chondroitin sulfate, heparin, or alginate, and proteins such as gelatin, collagen, fibrin, fibrinogen, albumin, or ovalbumin or copolymers or combinations thereof.

According to a particular embodiment the hydrogel comprises an extracellular matrix component (e.g. proteoglycans such as heparin sulfate, chondroitin sulfate, keratin sulfate, non-proteoglycan polysaccharide such as hyaluronic acid, collagen, elastin, fibronectin, laminin).

As used herein, "celluloses" includes cellulose and derivatives of the types described above; "dextran" includes dextran and similar derivatives thereof.

Other materials which can be used to form a hydrogel include alginates. Alginate is a carbohydrate polymer isolated from seaweed, which can be crosslinked to form a hydrogel by exposure to a divalent cation such as calcium as described, for example, in WO 94/25080, the entire disclosure of which is incorporated herein by this reference. Alginate is ionically crosslinked in the presence of divalent cations, in water, at room temperature, to form a hydrogel matrix. Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemically modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or epsilon-caprolactone. The resulting polymer includes alginate blocks which permit ionically catalyzed gelling, and oligoester blocks which produce more rapid degradation depending on the synthetic design. Alternatively, alginate polymers may be used wherein the ratio of mannuronic acid to guluronic acid does not produce a film gel and the alginate polymers may be derivatized with hydrophobic, water-labile chains, e.g., oligomers of epsilon-caprolactone. The hydrophobic interactions induce gelation, until they degrade in the body.

Additionally, polysaccharides which gel by exposure to monovalent cations, including bacterial polysaccharides such as gellan gum, and plant polysaccharides such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a nonion, such as mannitol, and then injected to form a gel.

Polysaccharides that are very viscous liquids or are thixotropic, and form a gel over time by the slow evolution of structure, may also be useful. For example, hyaluronic acid, which forms an injectable gel with a consistency like a hair gel, may be utilized. Modified hyaluronic acid derivatives may be particularly useful. As used herein, the term "hyaluronic acids" refers to natural and chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and derivatives thereof are available from Genzyme, Cambridge, Mass. and Fidia, Italy.

Other polymeric hydrogel precursors which may be utilized include polyethylene oxide-polypropylene glycol block copolymers such as PLURONICS™ or TETRONICS™, which are crosslinked by hydrogen bonding and/or by a temperature change, as described in Steinleitner et al., Obstetrics & Gynecology, vol. 77, pp. 48-52 (1991); and Steinleitner et al., Fertility and Sterility, vol. 57, pp. 305-308 (1992). Other materials which may be utilized include proteins such as fibrin, collagen and gelatin. Polymer mixtures may also be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) can be combined to form a gel over the course of time, e.g., as quickly as within a few seconds.

Exemplary polysaccharides contemplated for the hydrogels of the present invention include, but are not limited to chitin, agar, cellulose, starch, dextran, glucan, chitosan, alginate and hyaluronic acid. Thus, for example, the agent may be an alginate an agar or a chitosan.

According to another embodiment, the hydrogels are fabricated from synthetic polymers. Examples of synthetic polymers include, but are not limited to poly(urethanes), poly (siloxanes) or silicones, poly(ethylene), poly(ethylene) glucol (PEG), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolid-es) (PLGA), polyanhydrides, and polyorthoesters.

According to yet another embodiment, the hydrogels comprise minerals. Examples of minerals that may be used in the hydrogels of the present invention include, but are not limited to calcium, magnesium, boron, zinc, copper, manganese, iron, silicon, selenium, phosphorus and sulfur.

According to a particular embodiment, the hydrogel comprises at least one of matrigel, collagen or fibrin.

According to another embodiment, the hydrogel comprises PEG. Contemplated PEG hydrogels include, but are not limited to PEG-fibrinogen, PEG-gelatin, PEG-collagen and PEG laminin. Methods of encapsulating the neural cells on to the hydrogel are known in the art—see for example Khetan, S., Burdick, J. Cellular Encapsulation in 3D Hydrogels for Tissue Engineering. *J. Vis. Exp.* (32), e1590, doi:10.3791/1590 (2009), and Nicodemus et al., Tissue Eng Part B Rev. 2008 June; 14(2):149-65, the contents of both are incorporated herein by reference.

It will be appreciated that if the cells are derived from a tissue (and not a cell line), the cells may be treated prior to encapsulation so as to remove non-cellular components. The cells may be treated with an enzyme such as collagenase, dispase or trypsin. Further methods may be used so that a single cell suspension of the cells is obtained (e.g. tituration and filtration).

The present embodiments also contemplate encapsulating additional cell types (i.e. a co-culture) in the hydrogels so as to increase neuronal development, survival and/or growth. For example, the present invention contemplates encapsulating endothelial cells (e.g. HUVEC cells) or fibroblast cells together with the neuronal cells in the hydrogels (see for example Caspi et al., Circ Res. 2007 Feb. 2; 100(2):263-72. Epub 2007 Jan. 11; and Lesman et al., Ann N Y Acad. Sci. 2010 February; 1188:46-51 which describe co-culture of cardiac cells with endothelial cells and fibroblasts to increase survival of the graft).

Alternatively, tissue may be treated by chopping and/or cutting to the relevant size and encapsulated in the hydrogel without performing additional isolation steps.

Following encapsulation, the hydrogels of the present invention are preferably cultured in a medium which supports neural growth. Examples of such mediums are provided herein above.

According to a particular embodiment, the neural network is capable of surviving (and showing neuronal activity) ex vivo in the hydrogel for more than 30 days, more preferably more than 40 days, more preferably more than 50 days, more preferably more than 60 days, more preferably more than 70 days, more preferably more than 80 days, more preferably more than 90 days, more preferably more than 100 days.

While hydrogel medium 14 is illustrated in FIG. 1 as having a circular shape, this need not necessarily be the case, since it is not necessary for the hydrogel to be circular or spherical. Thus, hydrogel medium 14 can have any geometrical shape.

When neural network 10 serves as or is incorporated in an implantable scaffold, the material and shape of hydrogel medium 14 are selected for being implanted in the brain. Specifically, hydrogel 14 can be selected to have viscoelastic properties that match the viscoelastic properties of the host brain.

In various exemplary embodiments of the invention cells 12 are disconnected from any solid support having a shear modulus above 1 GPa, or above 100 MPa or above 10 MPa or above 1 MPa or above 100 kPa or above 10 kPa or above 1 kP. In some embodiments of the present invention cells 12 are disconnected from any solid support other than hydrogel medium 14. Preferably, at least 90% of cells are allowed to migrate or grow, individually, within medium 14 along any direction in the three-dimensional volume occupied by medium 14. These embodiments are different than situations in which the cells are attached to some rigid object such as a bead or the like, in which case the cells are not allowed to migrate at any direction since migration is prevented along those directions that pass through the rigid object. Thus, the present embodiments contemplate a neural network in which the neural cells reside, migrate and/or grow in a three-dimensional manner.

Figure 2:
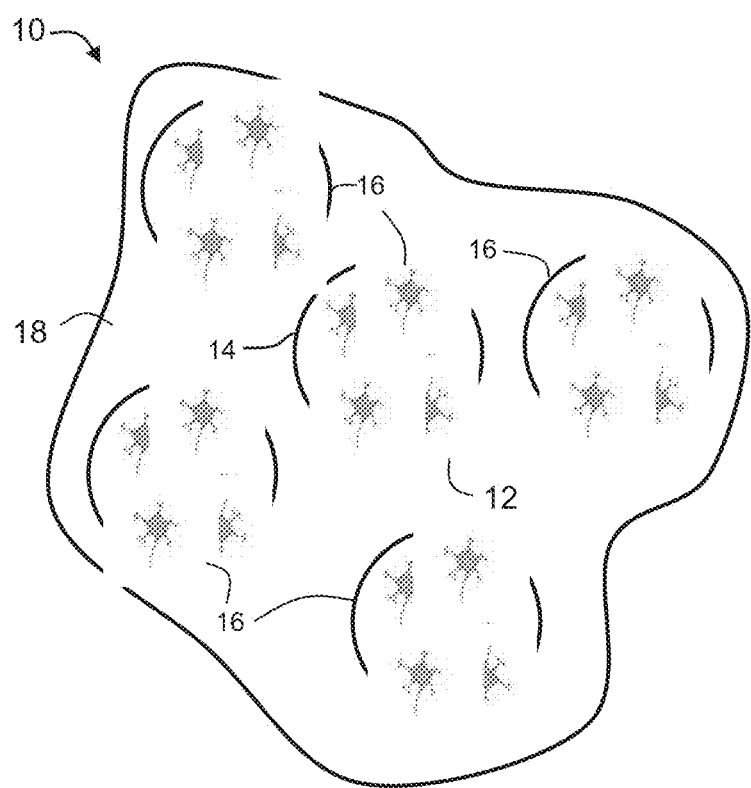

FIG. 2 is a schematic illustration of neural network 10, in embodiments of the present invention in which cells 12 are distributed in multiple non-overlapping islands 16 of hydrogel medium 14 within a second hydrogel medium 18. An image of network 10 in accordance with the present embodiments is provided in FIG. 18.

The shear modulus of medium 18 is preferably higher than the shear modulus of hydrogel medium 14, such that the neural cells of each island are spatially confined by hydrogel medium 18. Thus, the neural cells in each island 16 form a sub-network in neural network 10.

The shear modulus of medium 18 can be from about 70 Pa to about 100 KPa. In various exemplary embodiments of the invention the ratio between the shear modulus of medium 18 and the shear modulus of medium 14 is at least 2 or at least 2 or at least 3 or at least 4 or at least 5 or at least 6 or at least 7 or at least 8 or at least 9 or at least 10, or at least 11, or at least 12, or at least 13, or at least 14, or at least 15. In some embodiments, the ratio between the shear modulus of medium 18 and the shear modulus of medium 14 is at least 50, in some embodiments the ratio between the shear modulus of medium 18 and the shear modulus of medium 14 is at least 100, in some embodiments the ratio between the shear modulus of medium 18 and the shear modulus of medium 14 is at least 500, and in some embodiments the ratio between the shear modulus of medium 18 and the shear modulus of medium 14 is at least 1000.

Various methods are contemplated in order to ensure that the second hydrogel medium has sufficiently high shear modulus. For example, the present inventors contemplate increasing the shear modulus of the second hydrogel medium by increasing the amount of synthetic polymer (e.g., PEG) or protein (e.g. fibrinogen) therein.

Representative examples of materials suitable for the first hydrogel medium include, without limitation, Matrigel, Collagen or laminin based hydrogels or fibrin based hydrogel. Representative examples of materials suitable for the first hydrogel medium include, without limitation, PEG or any PEG base hydrogels such as PEG-Fibrinogen PEG-collagen and PEG-laminin.

Further details of regulating the shear modulus of a hydrogel are provided in Sarig-Nadir et al., 2008 Tissue Eng Part A. March;14(3):401-11.]]. The contents of which are incorporated herein by reference.

The advantage of the embodiments in which the cells are arranged in islands, each constituted a sub-network, is that each sub-network can serve as a structural object for the purpose of stimulation or sensing. Since such structural objects are larger than an individual neural cell, they can be accessed or stimulated at low resolution, thereby simplifying the interaction of the stimulating or retrieval system with neural network 10.

An additional advantage of this embodiment is that the survival probability of a sub-network which comprises a plurality of neural cells is higher than the survival probability of a single neural cell.

A typical volume of an island is, without limitation, from about 1 µl to about 4 ml. Lower volumes (e.g., from about 1 µl to about 100 µl) are preferred when network 10 is employed in vitro, and higher volumes (e.g., from 100 µl to about 4 ml) are preferred when network 10 is employed in vivo.

In embodiments in which hydrogel 18 is employed and neural network 10 serves as or is incorporated in an implantable scaffold, the material and shape of hydrogel medium 18 are preferably selected for being implanted in the brain. Preferably, hydrogel medium 18 is selected with sufficiently high shear modulus, so as to initially prevent neural cells from growing into medium 18. Nevertheless, a period of time following implantation of network 10 in the brain (e.g., a few days), hydrolysis and enzymatic processes in vivo generally matches the viscoelastic properties of medium 18 and neural cells are allowed to grow or migrate into medium 18.

Figure 3:
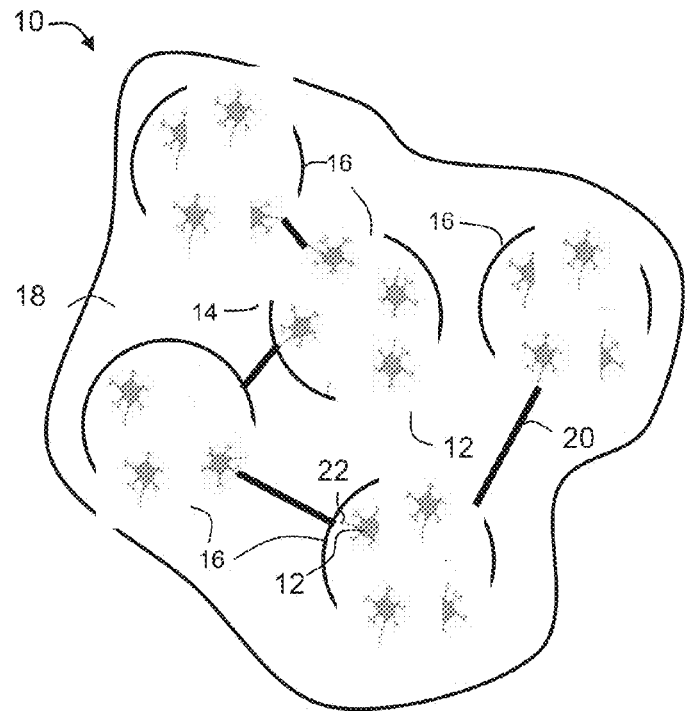

FIG. 3 is a schematic illustration of an embodiment of the invention in which one or more pair of islands is interconnected by a channel 20 formed in hydrogel medium 18. An image of network 10 in accordance with the present embodiments is provided in FIG. 19.

Channel 20 is optionally and preferably of micrometric diameter. For example, the diameter of channel 20 can be from about 0.5 µm to about 500 µm. The length of channel 20 equals at least the minimal distance between the islands it connects. This distance is typically from about 100 µm to about 10 mm. Shown in FIG. 3 are four channels but it is to be understood that it is not intended to limit the scope of the present invention to a network with four channels. Thus, network 10 can include any number of channels, including a single channel. Further, although FIG. 3 shows a configuration in which each island 16 is connected to one or two other channels, this need not necessarily be the case, since for some applications it may be desired to have at least one island that is connected to more than two other islands, and for some applications it may be desired to have at least one island that is not connected to any other island. Still further, although in FIG. 3 the connection between each pair of interconnected islands is via a single channel, the present embodiments contemplate configurations in which at least one pair of islands is interconnected via two or more channels.

Channel 20 can be formed in hydrogel 18 by a controlled ablation process, particularly, but not necessarily, a controlled focal photoablation process. In these embodiments, laser radiation, preferably in pulse mode, is focused onto hydrogel 18 while moving the focal point over hydrogel 18 along a path corresponding to the desired shape of the channel. The laser field causes an optical breakdown wherein plasma is formed by electron avalanche. This results in a discontinuous defect in the hydrogel structure. The intensity of the laser radiation is preferably selected above the characteristic optical breakdown threshold in hydrogel 18. For example, for a PEG based hydrogel, the intensity threshold is about $0.5 \times 10^{10}$ W/cm$^2$ for laser radiation at wavelength of 355 nm and pulse duration of 1 ns, and about $2.3 \times 10^{12}$ W/cm$^2$ for laser radiation at wavelength of 880 nm and pulse duration of 100 fs. Other laser parameters not excluded from the scope of the present invention.

In various exemplary embodiments of the invention channel 20 is occupied by an axon 22 of a respective neural cell 12. This allows communication between the respective pair of islands in the form of axon signals flowing over axon 22 through channel 20. It is appreciated that each channel can be occupied by more than one axon of a respective more than one neural cell.

The present embodiments contemplate a configuration in which the channel and axon are constituted to allow unidirectional flow of axon signals among pair of islands. This can be done by ensuring that the channel is occupied by one or more axons of cells residing in one island of the pair and devoid of any axon of cells residing in the other island of the pair. A representative procedure for forming a channel that ensures a unidirectional flow will now be described, with reference to FIGS. 4A-D.

Figure 4A:
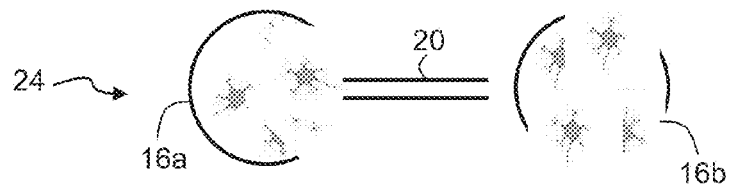
Figure 4B:
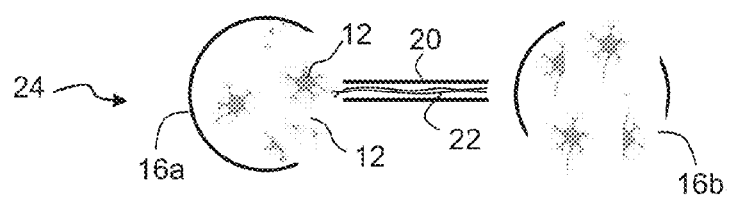

A channel 20 is formed, for example, by ablation, over a distance selected such that channel 20 is connected to a first island 16a of a pair 24 of islands, but not to a second island 16b of pair 24 (FIG. 4A). Thereafter, axon guidance conditions are generated within channel 20 such as to allow one or more axons 22 of cells 12 residing in island 16a to occupy channel 20. Since there is no fluid communication between channel 20 and island 16b the cells in island 16b cannot grow axons into channel 20 (FIG. 4B). The axon guidance conditions can be generated by supplying nutrition to the islands and incubating the pair 24 for a predetermined time period. Typically, the incubation period is a few (e.g., 2-20) days, but this period can also be less than 2 days or more than 20 days, depending on the length of channel 20.

Figure 4C:
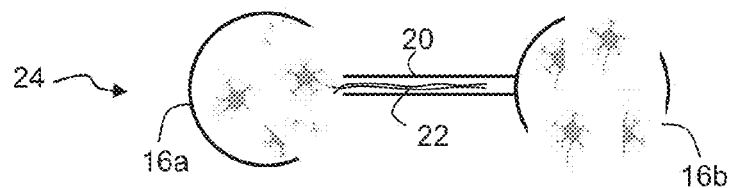
Figure 4D:
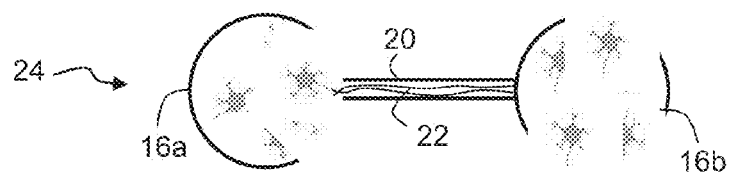

Once channel 20 is occupied by axon(s) 22, the channel is extended, for example, by continuing the ablation process to interconnect island 16a with island 16b (FIG. 4C). This allows further growth of axon(s) 22 into island 16b. Since channel 20 is already occupied by axons from island 16a, growth of axons from island 16b into channel 20 is suppressed.

A unidirectional growth of axons in channel 20 is advantageous from research as well as therapeutic standpoints. From research standpoint, such configuration allows a more detailed investigation of the neural communication within network 10 since the neural cell(s) that transmit the signal over the channel can be identified. From therapeutic standpoint, unidirectional guiding of neuronal connectivity can be used for creating predetermined connections between an implanted neural network and the host brain.

Reference is now made to FIG. 5 which is a schematic illustration of an implantable medical system 50, according to some embodiments of the present invention. System 50 comprises an implantable scaffold 52. Scaffold 52 can include the neural network of the present embodiments, for example, neural network 10 wherein hydrogel medium is adapted for being implanted in the brain 58 of a mammal, as further detailed hereinabove. System 50 can further include an optical device 54 implantable adjacently to scaffold 52 and having a light source 56 constituted for optically stimulating neural cells 12 of scaffold 52. In various exemplary embodiments of the invention device 54 is also configured for imaging neural cells 12 in vivo. Imaging is particularly useful when neural cells 12 are tagged, for example, by a detectable or reporter moiety, such as a fluorescent tag, so as to allow imaging their activity.

Following implantation in brain 58, at least some of the optogenetically modified neural cells 12 of scaffold 52 interact with the neurons 60 of brain 56. Device 54 can then be activated to emit stimulation light 62 directed to scaffold 52. The parameters of light 62 (for example, intensity, wavelength) are preferably selected to stimulate the optogenetically modified neural cells 12. In various exemplary embodiments of the invention device 54 emits pulsed light. In these embodiments, pulse rate, pulse duration and duty cycle are also selected to select to stimulate neural cells 12.

In some embodiments of the present invention system 50 comprises an electrode system 64 implantable in or adjacent to scaffold 52 and configured for receiving signals from neural cells 12 responsively to optical stimulation 62.

FIG. 6A is a schematic illustration of a system 70 suitable for stimulating nerves, according to some embodiments of the present invention. System 70 is particularly useful for in vitro stimulation. System 70 comprises a chamber 80 having therein a neural network, such as, but not limited to, neural network 10 described above. In various exemplary embodiments of the invention and an optical device 72 having one or more light sources 74 constituted for emitting light 76 to optically stimulate the neural cells (not shown) in neural network 10 of while being in chamber 80. Optical device is preferably also configured for imaging neural network 10. Imaging is particularly useful when neural cells 12 are tagged, for example, by a detectable or reporter moiety, such as a fluorescent tag, so as to allow imaging their activity.

In some embodiments of the present invention chamber 80 is configured to allow stimulating the neural cells from two opposite sides of chamber 80. For example, at least part of the top and bottom walls of chamber 80 can be can be made transparent to allow light 76 to enter chamber 80 both from above and below. In some embodiments of the present invention system 70 comprises an electrode system 78 positioned in chamber 80 adjacent to or in neural network 10 and configured for receiving signals from the neural cells responsively to the optical stimulation 76.

Chamber 80 is optionally and preferably configured both to incubate the neural cells and for allowing their stimulation. Thus, in some embodiments of the present invention chamber 80 comprises a microfluidic system (not shown, see FIG. 6B) which allows introducing nutrient supply and optionally also drugs or other substances to the neural network.

A representative example of a chamber 80 suitable for the present embodiments is illustrated in FIGS. 6B-D, where FIG. 6B illustrates an exploded view of chamber 80, FIG. 6C illustrates chamber 80 once assembled, and FIG. 6D illustrates a cross sectional view of chamber 80 along line A-A.

Hence, in some embodiments of the present invention chamber 80 comprises a microfluidic system 82 having a plurality of ports 84 and microchannels 86. For example, each microchannel can extend from an inlet port to an outlet port. Microchannels 86 are preferably distributed over an area selected sufficiently large so as to allow introducing different media contents to different neurons in the neural network.

Microfluidic system 82 is typically formed in a substrate, which can be a polymeric substrate. Suitable polymer substrate materials are generally selected based upon their compatibility with the manufacturing process (soft lithography, stereolithography and three-dimensional jet printing, etc.) and the conditions present in the particular operation to be performed by the microfluidic system. Such conditions can include extremes of pH, pressure within the microchannels, temperature, ionic concentration, and the like. Additionally, polymer substrate materials are also selected for their inertness to critical components of an analysis or synthesis to be carried out by the system. Polymeric substrate materials can also be coated with suitable materials, as known in the art.

The polymeric substrate material is preferably transparent to the stimulating light 76, to allow it to penetrate into chamber 80 through system 82. Alternatively, transparent windows of, e.g., glass or quartz, may be incorporated into the substrate. The polymer can have linear or branched backbones, and can be crosslinked or non-crosslinked.

Given the tremendous diversity of polymer chemistries, precursors, synthetic methods, reaction conditions, and potential additives, there is a large number of possible elastomer systems that are contemplated for fabricating the microfluidic system of the present embodiments.

Representative examples of polymers suitable for the present embodiments include, without limitation, polydimethylsiloxane (PDMS), PMMA, polycarbonate, polyisoprene, polybutadiene, polychloroprene, polyisobutylene, poly(styrene-butadiene-styrene), polyurethanes and silicones.

Chamber 80 also comprises a base structure 90 configured for holding neural network 10 therein. Base structure 90 can be made of any of the materials described above with respect to microfluidic system 82. For example, both microfluidic system 82 and structure 90 can be made of the same material. Base structure can be mounted on a support substrate 92, for example, a glass substrate.

In various exemplary embodiments of the invention chamber 80 comprises a porous membrane 88 positioned between microfluidic system 82 and base structure 90. The average pore size in membrane 88 can be from about 0.1 μm to about 2 μm. Representative examples of materials suitable for membrane 88, including, without limitation, Polytetrafluoroethylene (PTEE), polyethylene terephthalate (PET), and PDMS. In experiments performed by the present inventors, a Polytetrafluoroethylene (PTEE) membrane having an average pore size of about 0.4 μm was employed. Other types of membranes are not excluded from the scope of the present invention.

Membrane 88 serves a physical separator between neural network 10 and microfluidic system 82, while allowing exchange of fluid substances therebetween. In various exemplary embodiments of the invention microchannels 86 are provided as trenches with an open facet engaged by membrane 88, so as to facilitate fluid exchange between the microchannels 86 and neural network 10 through membrane 88.

The bottom layer 91 of base structure 90 is optionally and preferably exposed to the culture medium, e.g., for supplying of nutrients to cells in chamber 80.

In an exemplary embodiment, a well-like PDMS (DOW CORNING) base is produced and transferred to a glass substrate, optionally and preferably coated with glass nanoparticles (AEOSIL, EVONIC) so as to avoid irreversible bonding between PDMS and glass substrate. Neural cells suspended in a hydrogel matrix is then injected into the PDMS well to form a solid hydrogel network suspended in PDMS well. Thereafter the PDMS base incorporating suspended neuronal networks in a hydrogel matrix, the top PDMS layer and a porous membrane are assembled together in order to form a microfluidic chamber.

In use, fluid 94 containing one or more substances such as nutrition, chemical composition, drugs or the like is introduced from an external source (not shown) such as a manually or automatically operated pipette or a syringe into one or more inlet ports 84a of microfluidic system (FIG. 6D). Fluid 94 flows through microchannel 86 and perfuses through membrane 88 into neural network 10. Similarly, fluid present in neural network 10 perfuses in the opposite direction into microchannel 86. This fluid typically contains waste material secreted from the neural cells in neural network 10. Excess fluid 96 which contains some of fluid 94 and also the waste material exits chamber 80 through one or more outlet ports 84b. To ensure proper growth of neurons within the hydrogel network, culture medium 98 can be introduced, for example, via a culture medium port 97 formed in layer 91.

Reference is now made to FIGS. 7A-D which are schematic illustration of a chamber 100 according to some embodiments of the present invention. Chamber 100 can be substituted for chamber 80 of system 70 or it can be used as a standalone chamber. In various exemplary embodiments of the invention chamber 100 is employed for incubating neural network 10.

Chamber 100 is particularly useful for incubating cells which are distributed three-dimensionally in situations in which it is desired to access the cells optically. It was found by the present inventors that optical access is less accurate and difficult when the light path within the chamber includes air gaps. Yet, it is appreciated that vacuum conditions within an incubation chamber is inappropriate from cell viability standpoint.

In a search for a solution to this difficulty the present inventors devised a chamber which allows optical access devoid of air gaps in the optical path within the chamber while maintaining supply of air and optionally other gasses of fluids to the incubated cells. Broadly speaking, chamber 100 is designed and constructed such that the air is supplied to the cells from the sides of the chamber while the cells are optically accessed from above and/or below, preferably both from above and from below. In various exemplary embodiments of the invention the air is entrapped within a peripheral cavity at least partially surrounding the cell sample (e.g., neural network 10).

In various exemplary embodiments of the invention chamber 100 comprises an upper member 102 and a lower member 104 fittingly assembled in an air tight configuration, to prevent air from escaping or entering chamber 100 via the connection surfaces of members 102 and 104.

FIGS. 7A and 7B are schematic illustrations of a cross-sectional view (FIG. 7A) and a top view (FIG. 7B) of lower member 104, and FIGS. 7C and 7D are schematic illustrations of a cross-sectional view (FIG. 7C) and a top view (FIG. 7D) of upper member 102, according to some embodiments of the present invention. An image of the assembled chamber and an image of members 102 and 104 according to some embodiments of the present invention are shown in FIGS. 7E and 7F, respectively.

In some embodiments of the present invention lower member 104 comprises an inner cavity 106 for folding a biological sample (e.g., neural network 10), and a liquid culturing medium 108. Inner cavity 106 is surrounded by a wall 110 and is preferable central with respect to member 104. Optionally and preferably wall 110 is made circular, with threads 124 matching a screwing 126 on upper member 102 so that upper member 102 can be fitted to lower member 104 as a screw-on cap.

The biological sample is preferably placed in a recess 112 formed in the lower part of member 104. At least part of the lower part is preferably transparent to light. For example, the lower part can be made from glass or transparent polymer. In the illustration of FIGS. 7A and 7B recess 112 is in the center of a transparent window 114. In some embodiments of the present invention lower member 104 comprises a heating pad 116 which is preferably made annular and positioned circumferentially with respect to recess 112. Heating pad 116 is connected to a power source (not shown) by cables (shown in FIGS. 7E and 7F).

In various exemplary embodiments of the invention upper member 102 comprises a peripheral cavity 120 for holding gas supply to the biological sample. Cavity 120 has an inner wall 132 an outer wall 134 which can be concentric with respect to each other. To assemble chamber 100 member 102 is screwed onto member 104 such that there is fluid communication between cavity 120 and the periphery of medium 108, but recess 112 remains gas-free.

One or more ports 122 are formed in upper member to allow fluid (liquid and/or gas) exchange between cavity 120 and an external source (not shown). A transparent window 128 is optionally and preferably formed in upper member 102 at a location selected to overlays recess 112 of lower member 104 once members 102 and 104 are assembled together. In various exemplary embodiments of the invention upper member 102 is shaped to receive an objective lens of an imaging system such that the objective lens can be brought to engage or be in close proximity to window 128. In the representative example illustrated in FIG. 7C, upper member has a dent 136 defined by inner walls 132 opposite to cavity 120.

Chamber 100 allows the growing of cells for long periods of time while imaging the cultures. Chamber 100 allows maintaining controlled temperature, gas and liquid exchange and sterile environment for the cultures. A particular advantage of chamber 100 is that it allows optical access (e.g., for imaging and/or optical activation of neurons) both from the upper side (via window 128) and from the bottom side (via window 112), optionally and preferably simultaneously. This is allowed according to some embodiments of the present invention by preventing penetration of air to the volume between the sample and the respective window. In order to supply the sample the gas exchange needed for its survival, air contained in peripheral cavity 120 is exchanged with the culturing medium, but penetration of gas into the imaging area.

In some embodiments of the present invention temporal focusing is employed for stimulating and/or imaging neural cells 12. In temporal focusing, a temporal pulse manipulator is configured to affect trajectories of light components of an input pulse impinging thereon so as to direct the light components towards an optical axis of a lens along different optical paths. The temporal pulse manipulator unit is accommodated in a front focal plane of the lens, thereby enabling to restore the input pulse profile at the imaging plane. Temporal focusing allows to simultaneously illuminate a single line or a plane inside a volume of interest while maintaining optical sectioning.

The temporal focusing techniques can be utilized to simultaneously illuminate a single line or a plane inside a volume of interest, while maintaining optical sectioning by manipulating the laser pulse duration. It was found by the present Inventors that when this technique is applied to optical stimulation of three-dimensional neural network, the effectiveness of light-cell interactions is reduced since light scattering effects the light distribution, attenuate its power and scatter the emitted light.

In a search for an improved temporal focusing technique, the present inventors found that the efficiency and simplicity of the optical system can be significantly improved by employing on-axis temporal focusing.

FIG. 8 is a schematic illustration of a system 200 suitable for stimulating and/or imaging the neural network of the present embodiments.

System 200 comprises a temporal focusing system 202, characterized by an optical axis 204, and being configured for receiving a light beam 206. In the schematic illustration shown in FIG. 8, optical axis 204 is along the z direction, which is also referred to herein as the axial direction. The x- and y-directions which are orthogonal to the z direction are referred to collectively as the lateral directions.

Light beam 206 is in the form of a pulse or a pulse sequence or a plurality of pulse sequences. In various exemplary embodiments of the invention the pulse sequence is defined by two or more pulses having one or more identical characteristics, wherein the identical characteristic is/are selected from the group consisting of identical spectrum, identical duration and identical intensity. The pulse is preferably sufficiently short to generate nonlinear optical effects once light beam 206 interacts with a sample medium (not shown). A typical pulse width is, without limitation from a few hundreds of attoseconds to a few picoseconds. Typical single pulse energy is, without limitation, from about 10 nJ to a few (e.g., 10) mJ. Typical spectrum of light beam 206 is, without limitation in the red and near infrared spectral range (e.g., from about 600 nm to about 2.5 µm). Other characteristics for light beam 206 are not excluded from the scope of the present invention.

Temporal focusing system 202 controls the temporal profile of light beam pulse 206 to form an intensity peak at a focal plane 208, by virtue of the Fermat principle as further detailed hereinabove. Temporal focusing system 202 comprises a prismatic optical element 210 which receives light beam 206 from an input direction 12 parallel to or collinear with optical axis 204 and diffracts light beam 206 along input direction 12. Thus, light beam 206 continues according to the present embodiment continues on-axis through prismatic element 210, wherein the propagation direction of light beam 206 before and after the passage through prismatic element 210 is parallel or, more preferably collinear with optical axis 208 of temporal focusing system 202.

Prismatic element 210 can be a dual prism grating element, also known in the art as a "grism" element. A schematic illustration of prismatic element 210 suitable for some embodiments of the present invention is schematically illustrated in FIG. 9. In these embodiments, prismatic element 210 comprises two prisms 302 and 304 and a transmissive diffraction grating 306. In accordance with an embodiment of the invention, prism 302 is made of a material characterized by a refractive index $n_p$ and includes an angled surface 308 defined by an angle φ measured between surface 308 and a normal 310 to a base 312 of prism 302. Diffraction grating 306 is made of a material characterized by a refractive index $n_g$. Grating 306 can be, for example, a holographic grating.

The medium adjacent to element 210 can be air or any other material having a different refractive index $n_e$, which is different, preferably lower, than, $n_p$. For example, when system 202 operates in open air, the external medium is air and $n_e=1$. In some embodiments of the present invention diffraction grating 306 is separated from prisms 302 and 304 by a material having a refractive index $n_i$ other than $n_p$.

In operation, light beam 206 is incident on surface 308 of prism 302, for example, at an angle φ with respect to the normal surface 308 and is refracted into prism 302 at an angle set by Snell's law. Beam propagates in prism 302 to incident on grating 306. When grating 306 is separated from prisms 302 and 304 by a material $n_t$, beam 206 experiences another refraction event at the interface between $n_p$ and $n_t$ before arriving to grating 306. At grating 306 light beam 206 is diffracted according to the characteristic diffraction equation of grating 306, and according to the wavelength of the light. Thus, light rays of different wavelengths constituted in beam 206 are typically diffracted at different angles. In the schematic illustration of FIG. 9, three light rays, having wavelengths $\lambda_1$, $\lambda_2$ and $\lambda_3$, are illustrated, representing the highest, central and lowest wavelengths in beam 206, respectively. Each light ray propagates in prism 304 and is refracted out into the external medium $n_e$.

In various exemplary embodiments of the invention prismatic element 201 is symmetrical in that prism 304 is also be made of a material characterized by the same refractive index $n_p$ and also includes an angled surface defined by the same angle $\phi$. This allows the beam in and out of the grating 306 to be at the same angle (Littrow's angle) thus improving the efficiency of element 210 for any polarization.

The characteristics of element 210 ($n_p$, $n_g$, $\phi$) are selected according to the needs of the temporal focusing system 202. In various exemplary embodiments of the invention the characteristics of element 210 are selected such that for light rays having the central wavelength $\lambda_2$, the exit direction 213 is parallel or, more preferably collinear, with the entry direction 212 of beam 206.

Different choices of the prism material (e.g., glass, silicon or other high refractive index materials) and prism angle $\phi$ allow to a large extent customization of the output beam spread denoted $\Delta\theta_{eff}$ to match the requirements of system 202. The advantage of prismatic element 212 is the ability to achieve high spectral dispersion while maintaining forward beam propagation.

Referring now again to FIG. 8, temporal focusing system 202 optionally and preferably comprises a collimator 214 and an objective lens 216 aligned collinearly with respect to their optical axes. In these embodiments, prismatic optical element 210 is positioned so as to diffract the light beam onto collimator 214. Collimator 214 serves for redirecting at least some of the light rays exiting prismatic element 210 such that all the light rays exit collimator 214 parallel to each other. Collimator 214 can be, for example, a tube lens or the like. The objective 216 receives the parallel light rays and redirects them onto image plane 208. A cross-sectional view of the back aperture of objective 216 in the x-y plane is illustrated at 218.

Collimator 214 and objective 216 can be arranged as a telescope system. In various exemplary embodiments of the invention the distance between collimator 214 and objective 216 equals the sum of their focal lengths. The distance between the center of prismatic element 210 and collimator 214 can equal the focal length of collimator 214, and the distance between objective 216 and the focal plane 208 can, in some embodiments of the present invention equal the focal length of objective 216. Objective 216 can be allowed for reciprocal motion 220 along the z direction, so as to allow optical sectioning in different sample planes. However, this need not necessarily be the case, since the present Inventors discovered a technique for providing scanning of the optical sectioning plane without moving the objective. Thus, in some embodiments of the present invention objective lens 216 is at a fixed distance from collimator 214.

The present inventors found that the location of focal plane 208 can be controlled by the position of prismatic element 210 along the axial direction. The concept is schematically illustrated in FIG. 10. Shown in FIG. 10 are several positions of prismatic element 210 along the axial direction (the z direction in the present example). In the schematic illustration of FIG. 10, three equally-spaced positions of element 210 are shown, at z=−D, z=0 and z=+D, where D is an arbitrary number. It is to be understood that other positions are not excluded from the scope of the present invention. For each position, an intensity peak of the pulse is formed at a different distance from objective 216. The peaks are designated FP1, FP2 and FP3, corresponding to locations z=−D, z=0 and z=+D, respectively.

Thus, optical sectioning is achieved according to some embodiments of the present invention by varying the position of prismatic element 210 while maintaining a fixed position of objective 216 and, optionally also of collimator 214. This can be done using a movable stage 222 on which prismatic optical element 210 is mounted. Stage 222 is operative to move 224, preferably reciprocally, along the axial axis. The motion of stage 222 can be controlled by a controller 226. Optionally and preferably a data processor 242 communicates with controller 226 and provides timing for its operation.

In some embodiments of the present invention system 200 comprises a spatial manipulating optical system 228, positioned on the optical path of light beam 206 and aligned such spatial manipulating optical system 228 and temporal focusing system 202 are optically parallel or collinear with respect to their optical axes. Spatial manipulating optical system 228 preferably comprises at least one optical system 230 having a static optical axis for performing the spatial manipulation.

In some embodiments of the present invention optical system 230 comprises a spatial focusing system. These embodiments are useful when it is desired to utilize both temporal focusing of the illumination pulse and spatial focusing of this pulse along a lateral direction (e.g., the x and/or y axis). Thus, in the present embodiments, system 202 provides the temporal focusing while system 230 provides the spatial focusing along one or both lateral dimensions.

When it is desired to have spatial focusing only along one of the lateral dimension, static optical system can include an anamorphic lens arrangement, such as, but not limited to, a cylindrical lens.

While FIG. 8 illustrates an embodiment in which system 230 is before collimator 214 in terms of the light path, this need not necessarily be the same since, in some embodiments of the present invention system 230 can be interchanged with collimator 214. These embodiments are particularly useful when system 230 is a cylindrical lens.

In some embodiments of the present invention system 228 is also configured for laterally displacing the input light beam 206 along one of the lateral dimensions while directing the beam onto prismatic element 210 through optical system 230. When system 230 is a cylindrical lens, for example, a line image is produced. System 228 can comprise a dynamic optical system 232, such as, but not limited to, an arrangement of scanning mirrors for establishing the lateral displacement of beam 206. In embodiments of the invention in which the location of the focal plane along the axial direction is controlled by varying the position of prismatic element 210, the displacement of prismatic element optionally and preferably is accompanied by a displacement of optical 230 optionally and preferably without changing the direction of its optical axis. Preferably, the distance between prismatic element 210 and system 230 along the axial direction is fixed at all times. This can be achieved by mounting both prismatic element 210 and system 230 on a rigid support structure (not shown) connected to stage 222.

Also contemplated, are embodiments in which the temporal focusing is employed to excite a two-dimensional pattern. In these embodiments, system 230 optionally and preferably comprises an optical patterning system, such as, but not limited to, a spatial light modulator (SLM), and a digital light projector which generates the pattern. The optical patterning system can be position to illuminate the pattern on prismatic element 210. The temporal focusing system images this pattern onto the focal plane 208, while maintaining optical sectioning and high quality illumination.

In various exemplary embodiments of the invention the optical patterning system is transmissive, in which case the light preferably continues on axis while passing through the optical patterning system. In some embodiments, the optical patterning system is made reflective, in which case the light is redirected before it arrives at element 210. Also contemplated, are embodiments in which the optical patterning system is reflective but is positioned such that the deflection of the light beam due to the interaction with the optical patterning system is small (e.g., less than 10 degrees, or less than 5 degrees, or less than 3 degrees, or less than 2 degrees). For example, an SLM can be positioned such that its reflective plane is at a small angle (e.g., less than 10 degrees, or less than 5 degrees, or less than 3 degrees, or less than 2 degrees) to axis 204.

Further contemplated, are embodiments in which the temporal focusing is employed in a wide-field illumination, in which case a cylindrical lens it is not required. In these embodiments, lens arrangement 230 optionally and preferably comprises a spherical lens.

In some embodiments of the invention, a large magnification telescope (for example, magnification of at least 40× or at least ×50 or at least ×60 or at least ×100 or at least ×200 or at least ×300 or at least ×400, preferably, but not necessarily up to ×500) and a high numerical aperture objective (for example, NA of at least 0.5 or at least 0.75, e.g., 1) is incorporated in system 200. These embodiments allow illuminating a small shape (e.g., short line), which is relatively robust to scattering. The advantage of this embodiment is that it provides both spatial and temporal focusing which can be useful in many applications, including, without limitation, single cell manipulation and/or stimulation, and depth imaging with reduced or eliminated out-of-focus excitation. The out-of-focus excitation is reduced or eliminated since the temporal focusing effect reduces or prevents effective two-photon excitation near the tissue surface.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

General Materials And Methods

Preparation of 3D Neural Cultures:
Embryonic Primary Cultures:
A pregnant Sprague Dawley rat (E18) was sacrificed, embryos were removed and brains were extracted. Cortical region of the brains were separated in cold PBS containing 20 mM glucose and diced into small pieces. Tissue was manually titurated by transferring the tissue and liquid few times through a pipette. The solution containing the cells was filtered using a 70 μm cell strainer (Biologix), centrifuged and the cells were resuspended.

Postnatal Primary Cultures:

Newborn (P0-P3) rats were sacrificed and brains were extracted. Cortical region of the brains were separated in cold PBS containing 20 mM glucose and diced into small pieces. Neural cells were dissociated from the tissue by incubation of 10-15 minutes in Trypsin (sigma) in 37 degrees Celsius with shaking. Fetal bovine serum was added and tissue was manually titurated by transferring the tissue and liquid few times through a pipette. The solution containing the cells was filtered using a 70 μm cell strainer (Biologix), centrifuged and the cells were resuspended.

For both postnatal and embryonic cultures, the cells were counted and 2 million cells were encapsulated in 50 μl Matrigel scaffold (BD Biosciences). Culturing media was composed of Minimal Essential Media (MEM, Sigma) containing 100 μl/ml of NU Serum (BD Biosciences), 0.3 g/ml of L-Glutamine (Sigma), 1:500 B-27 supplement (Gibco), 50 ngr/ml of Nerve Growth Factor (NGF, Alomone labs), 10 ngr/ml of Brain-Derived Neurotrophic Factor (BDNF, R&D systems), 25 μgr/ml of Insulin (Sigma), and 2 μgr/ml of Gentamicin. Half volume of culturing media was replaced twice a week.

Viability Testing:

A Phosphate buffered saline (PBS) solution containing 2 μl/1 ml of Ethidium homodimer (Sigma), a nucleic acid fluorescent tag designed to stain dead cells red, 0.2 μl/1 ml of calcien (Sigma), which stains live cells green and 2 μl/1 ml of 4',6 diamidino-2-phenylindole (DAPI), a fluorescent tag engineered to stain the nuclei of all cells blue was added to the 3D cultures. Cultures were incubated for 1 hour in 37 degrees Celsius with shaking. The cultures were washed and then visualized using a fluorescent microscope (Nikon) or a 2-photon laser microscope (Spectra Physics) and photographs were captured or a confocal microscope (LSM 700, Zeiss). Imaris software (Bitplane) was used to automatically count the cells/nuclei in 2D or 3D. The counts of the live cells, dead nuclei and total nuclei in each photograph were used to calculate the vitality percentage for each sample.

Immunostaining:

Cultures were fixed for 2 hours using a 4% Paraformaldehyde (PFA) solution in PBS, followed by 2 hours of permeabilization and a blocking process in 0.3% Triton and 4% Fetal Bovine Serum (FBS) solution in PBS. The cultures were washed, and the primary antibodies, 1:400 concentration Mouse-Anti Beta III Tubulin (Promega), a marker of neuronal cells, and 1:200 concentration Rabbit-Anti S100 (Sigma), a marker of glial cells, were added, and the cultures were incubated over-night at 4° C. The cultures were washed and secondary antibodies, 1:100 concentration CY 3 Conjugated Goat-Anti-Mouse Immunoglubluin (Jackson) and 1:100 concentration Dylight 488 Conjugated Goat-Anti-Rabbit IgG (Jackson), were added along with 1:500 DAPI (Sigma), designed to stain the nuclei of all cells. The cultures were washed and then visualized using a fluorescent microscope (Nikon) or a confocal microscope (LSM 700, Zeiss).

Results

In order to create a mammalian 3D model of the central nervous system, the present inventors tested the ability of cortical tissue and cortical dissociated cells from both postnatal rats to form a viable neural network. As illustrated in FIGS. 11A-F, all biological models showed spreading of the cells and creation of a 3D network. The viability rate of the network in all three models was high, as demonstrated by Calcein staining (FIGS. 11A-C) that stains live cells green, and Ethidium homodimer staining (FIGS. 11D-F) that stains the nuclei of dead cells red.

The present inventors further showed that the neural networks could be maintained in the hydrogel for 65 days. As illustrated in FIG. 12A-C, following 65 days of culture, the neural network displayed a high viability rate as demonstrated by Calcein staining (FIG. 12A) that stains live cells green, by Ethidium homodimer staining (FIG. 12B) that stains the nuclei of dead cells red and by DAPI staining that stains the total nuclei of the cells blue (FIG. 12C).

FIG. 21 illustrates that neural networks of primary cells can be maintained in the hydrogel for up to 49 days.

At the start of the process, about 80% of the cells survive the process of dissociation from the tissue. After the first day, survival decreased to 68%. Starting from day 14, it can be seen that about 95% of the cells survived (probably due to the supporting action of the glial cells).

The present inventors illustrated that Matrigel encapsulated neural networks could be genetically modified to express a calcium indicator—GcaMP3. As illustrated in FIGS. 13A-C, the viral agent was able to penetrate and transfect the network to the depth of the scaffold. Changes in fluorescence intensity of the indicator resulting from neuronal spontaneous activity were observed.

FIG. 14A illustrates rapid 3D functional microscopy of the neural network of Matrigel encapsulated cells. The 3D neural network was stained with organic calcium indicators or transfected with a viral agent for a genetically encoded calcium indicator Fluo-4. Using a temporal focusing based custom made optical system, a 3D volume of 250×500×200 μm [X×Y×Z] in a frame rate of up to 200 frames/sec, which are up to 20 volumes/sec was acquired. A volumetric representation of the cellular content of the 3D network and the fluorescence intensity changes of the indicator was created. The electrically active neurons are represented by white spheres and the non-electrically active cells, mostly glial cells, in black. Four representative patterns of the fluorescence intensity changes in different cells in the network are presented.

Transfection of Neural Cells:

As illustrated in FIG. 15A, 2D cultures of rat cortical dissociated cells were genetically modified to express the light gated channel, Channelrhodopsin2 (ChR2) and cultured on a multielectrode array. Upon optical stimulation, the cells were shown to be electrically active (FIG. 15B). Transfection of Matrigel encapsulated 3D cortical networks with the viral agent resulted in penetration of the viral agent to the depth of the scaffold and expression of ChR2 in the cells (FIG. 15C).

The present inventors further contemplate using a 3D optical stimulation system using holography. The system will contain a spatial light modulator (SLM) device and will be able to create specific 3D light patterns, allowing for optical stimulation of a specific cell or multiple cells in the 3D scaffold (FIG. 15D). Combining this method of stimulation with the optical imaging method described above, will allow the simultaneous stimulation of the network and recording of the propagation of the resulted network activity in 3D.

Ablation:

FIG. 16 illustrates how a Matlab based application may be used to allow for the planning and accurate automatic execution of a 2D (FIG. 16A) or 3D (FIG. 16C) ablation patterns. One picture (FIG. 16A) or representation of stack of pictures (FIG. 17) may be acquired for the planning of the ablation pattern. FIG. 16B demonstrates the directed growth of postnatal cortical tissue originated from rat and encapsulated in a hydrogel scaffold, into the designed ablation pattern. FIG. 19 is a photograph of two cortical tissues originating from postnatal rats embedded in PEGylated Fibrinogen hydrogel showing directional growth into the amplified femtosecond laser ablated microchannels and the creation of physical connection between the two tissues.

Further Immunostaining Studies:

Rat cortical dissociated cells were encapsulated in Matrigel scaffold and stained by whole gel immunostaining using antibodies that recognize glial cells (S100) and neuronal cells (βIII tubulin). Total nuclei were stained with Dapi. The viability rate of the network was determined using a whole-gel staining using Calcein AM and ethidium. As illustrated in FIGS. 20A-D, the cortical cells generated dense networks and stained positive for glial cells and neuronal cells throughout the whole depth of the scaffold.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A neural network, comprising a plurality of optogenetically modified neural cells being three-dimensionally distributed in a first hydrogel medium and being disconnected from any solid support having a shear modulus above 1 GPa; wherein said cells are distributed in at least one island of said first hydrogel medium within a second hydrogel medium having a shear modulus which is higher than a shear modulus of said first hydrogel medium, and wherein neural cells of said at least one island are spatially confined by said second hydrogel medium.

2. The neural network of claim 1, wherein said first hydrogel medium comprises extracellular matrix (ECM) proteins.

3. The neural network of claim 1, wherein said nerve cells are not comprised in a tissue.

4. The neural network of claim 1, wherein there are multiple non-overlapping islands of said first hydrogel medium within said second hydrogel medium, thus forming a sub-network.

5. The neural network of claim 4, wherein at least one pair of islands is interconnected by a channel formed in said second hydrogel medium.

6. The neural network of claim 5, wherein said channel is occupied by at least one axon of at least one neural cell.

7. The neural network of claim 6, wherein said channel and said at least one axon are constituted to allow unidirectional flow of axon signals among said pair of islands.

8. An implantable scaffold, comprising the neural network according to claim 1, wherein said hydrogel medium is adapted for being implanted in the brain of a mammal.

9. An implantable medical system, comprising an implantable scaffold having the neural network according to claim 1, and an optical device implantable adjacently to said scaffold and having a light source constituted for optically stimulating said neural cells in vivo.

10. The system according to claim 9, wherein said optical device is configured also for imaging an activity of said cells.

11. A system for stimulating neural cells, comprising a chamber having therein the neural network according to claim 1, and an optical device having a light source constituted for optically stimulating and/or imaging said neural cells while being in said chamber.

12. The system according to claim 11, wherein said chamber is configured to allow stimulating and/or imaging said neural cells from two opposite sides of said chamber.

13. The system according to claim 11, further comprising an electrode system positioned in said neural network and configured for receiving signals from said neural cells responsively to optical stimulation of said neural cells by said optical device.

14. A system for drug screening, comprising:
a chamber having therein the neural network according to claim 1,
a microfluidic system for supplying at least one drug to said cells; and
an imaging device constituted for imaging an activity of said neural cells while being in said chamber.

15. The system according to claim 14, wherein said chamber is configured to allow imaging said neural cells from two opposite sides of said chamber.

16. The system according to claim 14, further comprising an electrode system positioned in said neural network and configured for receiving signals from said neural cells responsively to optical stimulation of said neural cells by said optical device.

17. The system of claim 14, wherein said microfluidic system is constituted for supplying different drugs to different regions of said neural network.

18. A method of producing a neural network, comprising:
introducing a plurality of neural cells into a first hydrogel medium to form a three-dimensional distribution of said neural cells disconnected from any solid support having a shear modulus above 1 GPa;
introducing said first hydrogel medium into a second hydrogel medium having a shear modulus which is higher than a viscosity of said first hydrogel medium, to form at least one island of said first hydrogel medium within said second hydrogel medium; and
optogenetically modifying said neural cells.

19. The method of claim 18, wherein there are multiple non-overlapping islands of said first hydrogel medium within said second hydrogel medium, and the method further comprising forming a channel in said second hydrogel medium so as to interconnect a pair of islands by said channel.

20. The method of claim 19, further comprising generating axon guidance conditions within said channel such as to allow at least one axon of said cells to occupy said channel.

21. The method of claim 19, wherein said forming said channel comprises:
forming said channel over a distance selected such that said channel is connected to a first island of said pair but not to a second island of said pair;
generating axon guidance conditions within said channel such as to allow at least one axon of cells of said first island to occupy said channel; and
extending said channel to interconnect said first island to said second island to allow further growth of said least one axon into said second island.

22. A neural network, comprising a plurality of optogenetically modified neural cells being three-dimensionally distributed in a first hydrogel medium and being disconnected from any solid support having a shear modulus above 1 GPa, wherein said first hydrogel medium is within a medium having a shear modulus which is higher than a shear modulus of said first hydrogel medium, and wherein said neural cells are spatially confined by said second medium.

23. A system for stimulating neural cells, comprising the neural network according to claim 1, and an optical device having a light source constituted for optically stimulating and/or imaging said neural cells.

* * * * *